(12) United States Patent
Dobson et al.

(10) Patent No.: US 8,524,861 B2
(45) Date of Patent: Sep. 3, 2013

(54) TREATMENT OF BACTERIAL INFECTIONS

(75) Inventors: Curtis Dobson, Manchester (GB); Keith Alan Crutcher, Cincinnati, OH (US)

(73) Assignee: AI2 Limited, Manchester (GB)

( * ) Notice: Subject to any disclaimer, the term of this patent is extended or adjusted under 35 U.S.C. 154(b) by 1179 days.

(21) Appl. No.: 10/586,416

(22) PCT Filed: Feb. 28, 2005

(86) PCT No.: PCT/GB2005/000769
§ 371 (c)(1),
(2), (4) Date: Aug. 28, 2008

(87) PCT Pub. No.: WO2005/082399
PCT Pub. Date: Sep. 9, 2005

(65) Prior Publication Data
US 2009/0169598 A1    Jul. 2, 2009

(30) Foreign Application Priority Data

Feb. 27, 2004    (GB) .................................. 0404374.1

(51) Int. Cl.
C07K 7/08    (2006.01)
(52) U.S. Cl.
USPC ............ 530/326; 530/324; 530/325; 514/2.4; 514/21.4; 514/21.5
(58) Field of Classification Search
USPC ................ 530/326, 324, 325; 514/2.4, 21.4, 514/21.5
See application file for complete search history.

(56) References Cited

U.S. PATENT DOCUMENTS

| | | | |
|---|---|---|---|
| 7,691,382 B2 | 4/2010 | Dobson | |
| 8,017,579 B2 | 9/2011 | Dobson | |
| 2002/0164789 A1 | 11/2002 | Laskowitz et al. | |
| 2005/0208078 A1 | 9/2005 | Hoffman et al. | |
| 2005/0260581 A1* | 11/2005 | Fontana et al. ................ | 435/6 |
| 2005/0266017 A1 | 12/2005 | Druilhe et al. | |
| 2007/0117746 A1 | 5/2007 | Dobson | |
| 2008/0207508 A1 | 8/2008 | Dobson | |
| 2009/0048171 A1 | 2/2009 | Dobson | |
| 2010/0221273 A1 | 9/2010 | Dobson | |
| 2012/0258907 A1 | 10/2012 | Dobson | |

FOREIGN PATENT DOCUMENTS

| | | |
|---|---|---|
| WO | 9201462 A1 | 2/1992 |
| WO | 9404177 | 3/1994 |
| WO | 9842751 | 10/1998 |
| WO | 9937664 A1 | 7/1999 |
| WO | 9945950 A2 | 9/1999 |
| WO | 0215923 | 2/2002 |
| WO | 03026479 | 4/2003 |
| WO | 2003052076 | 6/2003 |
| WO | 2005039534 | 5/2005 |
| WO | WO2005/058959 | 6/2005 |
| WO | WO2005/061539 | 7/2005 |
| WO | 2005082399 | 9/2005 |
| WO | 2007000584 | 1/2007 |

OTHER PUBLICATIONS

Motizuki, Mitsuyoshi (Biochemical Journal 342(1), 215-221, 1999).*
U.S. Appl. No. 13/335,549 Restriction Requirement dated Aug. 30, 2012.
U.S. Appl. No. 10/580,984 Notice of Allowance dated Jun. 2, 2011.
U.S. Appl. No. 13/335,549 Non-Final Office Action dated Nov. 14, 2012.
Moerman et al. Antibacterial and antifungal properties of x-helical, cationic peptides in the venom of scorpions from southern Africa. Eur. J. Biochem. (2002). 269:4799-4810.
Muller et al. Antimicrobial peptides as potential new antifungals. Mycoses (1999) 42:Suppl 2: 77-82. Abstract.
Vogel et al. Towards a structure-function analysis of bovine lactoferricin and related tryptophan- and arginine- containing peptides. Biochem. Cell. Biol. (2002). 80(1):49-63. Abstract.
U.S. Appl. No. 12/702,919 Restriction Requirement dated Dec. 14, 2011.
U.S. Appl. No. 12/702,919 Non-Final Office Action dated Mar. 21, 2012.
Hamy et al. An inhibitor of the Tat/TAR RNA interaction that effectively suppresses HIV-1 replication. Proc. Natl. Acad. Sci. USA (1997). 94:3548-3553.
Clay, et al. "Localization of a Domain in Apolipoprotein E with both cytostatic and cytotoxic activity," Biochemistry, 1995:34; 11142-11151.
Gait, et al. "Progress in anti-HIV structure-based drug design," TIBTECH, Oct. 1995: vol. 13, 430-438.
Olsson, et al. "Possible functional interactions of Apolipoprotein B-100 segments that associate with cell proteoglycans and the ApoB/E receptor," Arterioscler. Thromb. Vasc. Biol. 1997: 17; 149-155.
Hirsch, et al. "Antiretroviral drug resistance testing in adults with HIV infection: implications for clinical management," JAMA 1998: 279 (24); 1984-1991.
Wang, et al. "Apolipoprotein E (ApoE) peptide regulates tau phosphorylation via two different signaling pathways," J. Neurosci. Res. 1998: 51; 658-665.
U.S. Appl. No. 10/580,761 Office Action dated Jan. 9, 2008.
U.S. Appl. No. 10/580,761 Office Action dated Jun. 24, 2008.

(Continued)

*Primary Examiner* — David Lukton
(74) *Attorney, Agent, or Firm* — Linda B. Huber; Nixon Peabody LLP

(57) ABSTRACT

The invention relates to polypeptides, comprising repeats of peptides derived from apolipoproteins, which exhibit antibacterial activity and to nucleic acids encoding the same. The invention further provides the use of such polypeptides, derivatives, analogues or nucleic acids as medicaments, and also their use in methods of preventing or treating bacterial infection or objects and surfaces. The invention further extends to objects, such as contact lenses, coated with the polypeptides.

29 Claims, 8 Drawing Sheets

(56) References Cited

OTHER PUBLICATIONS

U.S. Appl. No. 10/580,761 Office Action dated Nov. 26, 2008.
U.S. Appl. No. 10/580,761 Office Action dated Jun. 9, 2009.
U.S. Appl. No. 10/580,761 Notice of Allowance dated Nov. 2, 2009.
U.S. Appl. No. 10/580,984 Office Action dated Jun. 25, 2009.
U.S. Appl. No. 10/580,984 Office Action dated Dec. 22, 2009.
U.S. Appl. No. 10/580,984 Office Action dated Jun. 30, 2010.
U.S. Appl. No. 10/580,984 Office Action dated Dec. 3, 2010.
Owens, et al. "Apolipoprotein A-I and its amphipathic helix peptide analogues inhibit human immunodeficiency virus-induced syncytium formation," J. Clin. Invest., Oct. 1990: vol. 86; 1142-1150.
PCT/GB04/05360 ISR dated Oct. 4, 2005.
PCT/GB04/05360 Written Opinion dated Oct. 4, 2005.
PCT/GB04/05360 IPRP dated Jun. 20, 2006.
PCT/GB04/05438 ISR dated Oct. 4, 2005.
PCT/GB04/05438 Written Opinion dated Oct. 4, 2005.
PCT/GB04/05438 IPRP dated Jun. 26, 2006.
PCT/GB06/02350 ISR dated Dec. 1, 2006.
PCT/GB06/02350 Written Opinion dated Dec. 1, 2006.
PCT/GB06/02350 IPRP dated Jan. 9, 2008.
PCT/GB05/00769 ISR dated Oct. 18, 2005.
PCT/GB05/00769 Written Opinion dated Oct. 18, 2005.
PCT/GB05/00769 IPRP dated Aug. 30, 2006.
U.S. Appl. No. 11/916,627 Office Action dated Dec. 24, 2009.
U.S. Appl. No. 11/916,627 Office Action dated May 10, 2010.
U.S. Appl. No. 11/916,627 Office Action dated Dec. 15, 2010.
Srinivas, et al. "Inhibition of virus-induced cell fusion by Apolipoprotein A-I and its amphipathic peptide analogs," J. Cellular Biochemistry, 1991: vol. 45; 224-237.
U.S. Appl. No. 11/916,627 Non Final Office Action dated Sep. 27, 2011.
Azuma et al., A Synthetic Peptide of Human Apoprotein E With Antibacterial Activity, Peptides, (2000), pp. 327-330, 21.
Boman et al., Antibacterial Peptides: Basic Facts and Emerging Concepts, Journal of Internal Medicine, (2003), pp. 197-215, 254.
Bradshaw, J.P., Cationic Antimicrobial Peptides, Issues for Potential Clinical Use, Biodrugs, (2003), pp. 223-240, 17(4).
Law et al., A Cross-Species Comparison of the Apolipoprotein B Domain That Binds to the LDL: Receptor, Journal of Lipid Research, (1990), pp. 1109-1120, 31.
Raffai et al., Molecular Characterization of Two Monoclonal Antibodies Specific for the LDL Receptor-Binding Site of Human Apolipoprotein E, Journal of Lipid Research, (1995), pp. 1905-1918, 36.

\* cited by examiner

Control      GIN 1p treated (i)                                                 (ii)

Figure 5
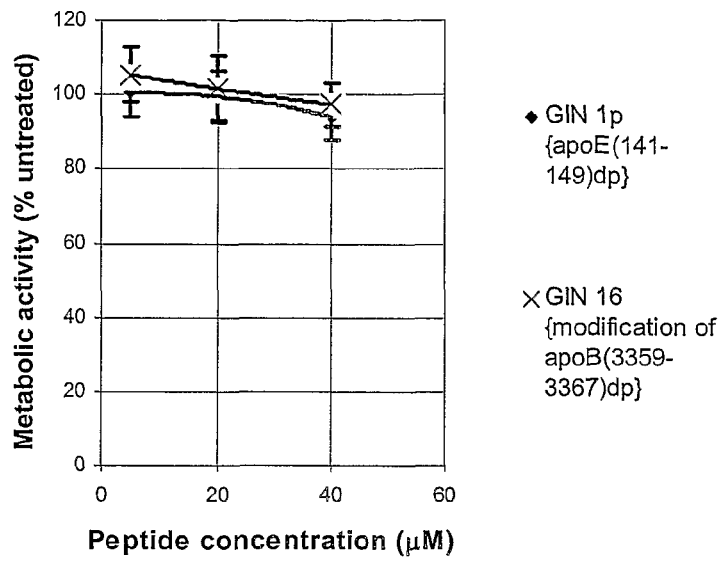
Figure 6A - GIN 1p
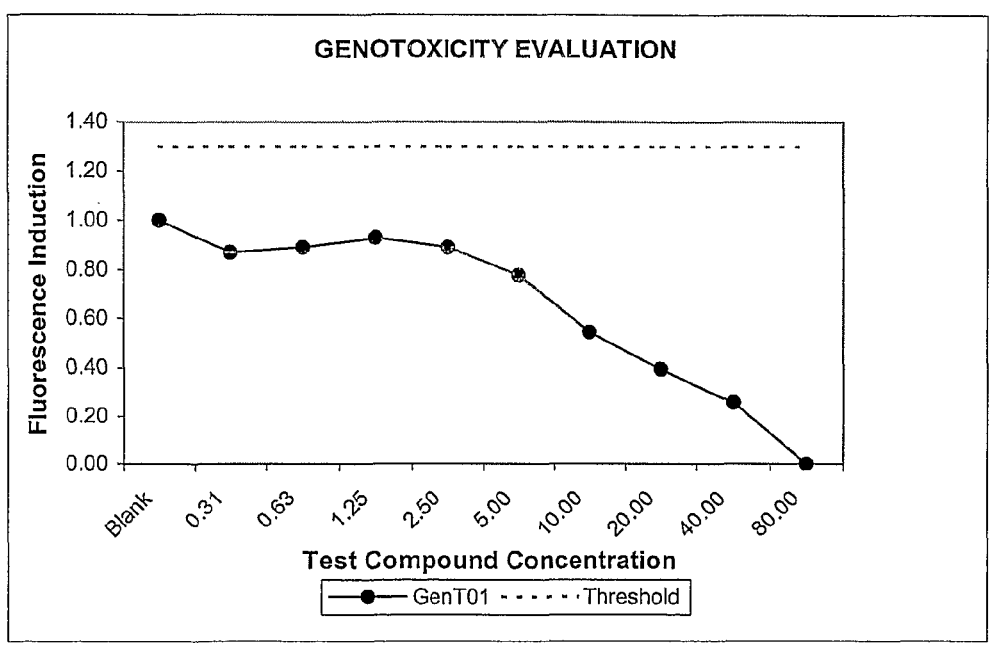

Figure 6B - GIN 33
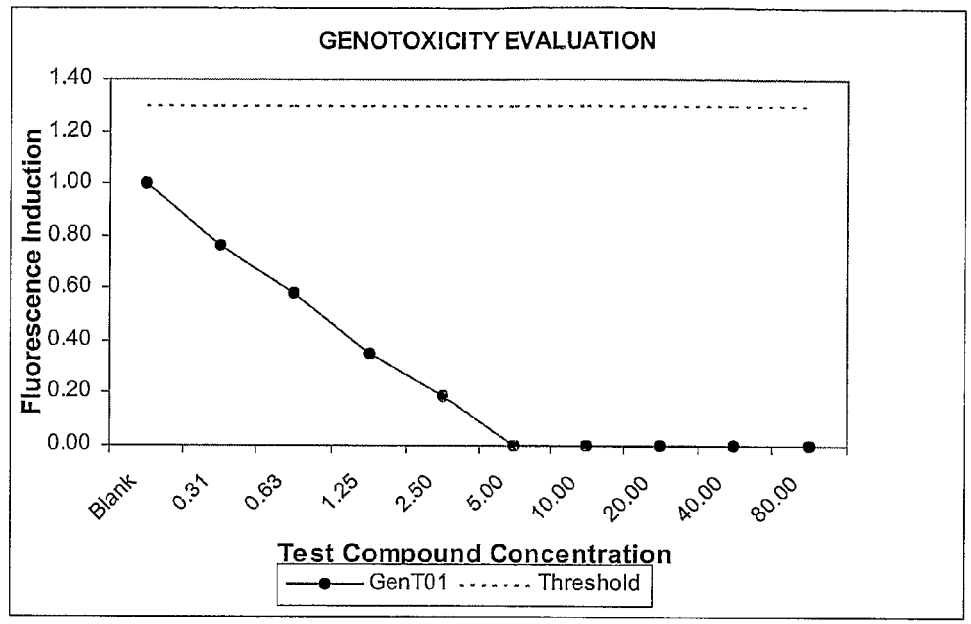
Figure 6C - GIN 34
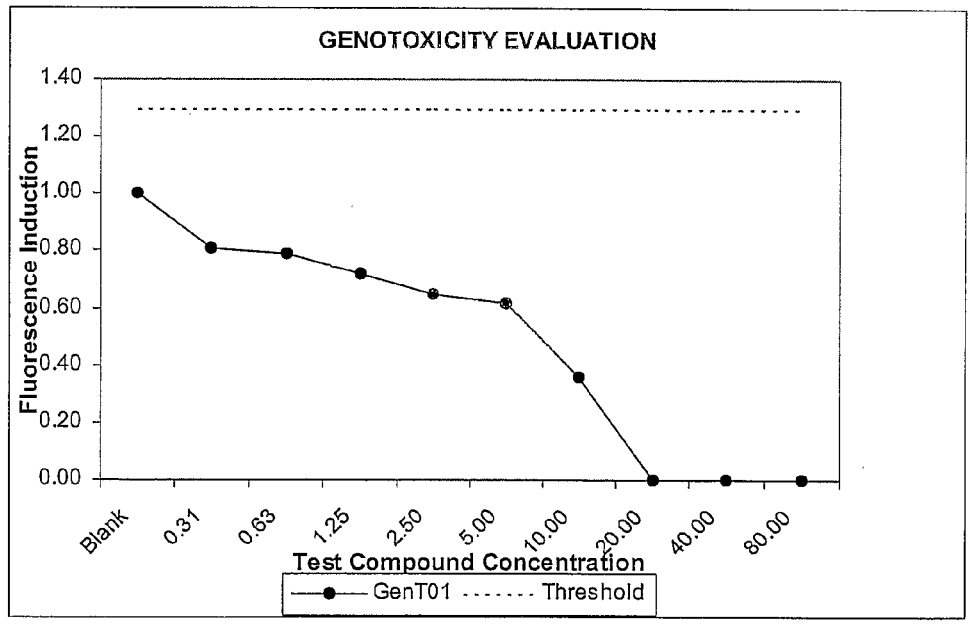

Figure 7
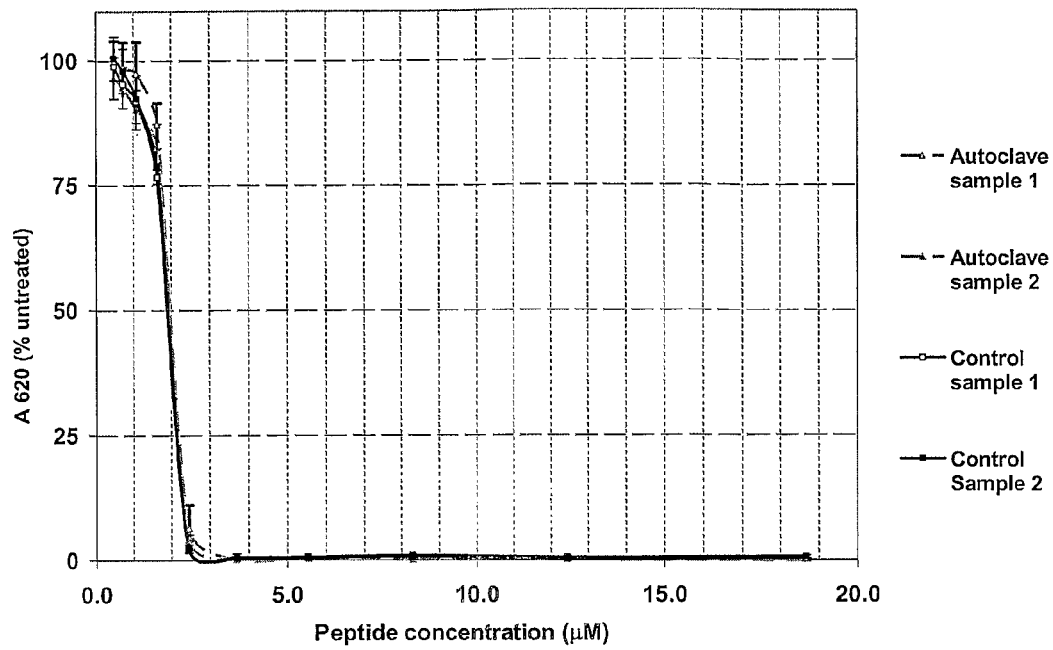
Figure 8
a)
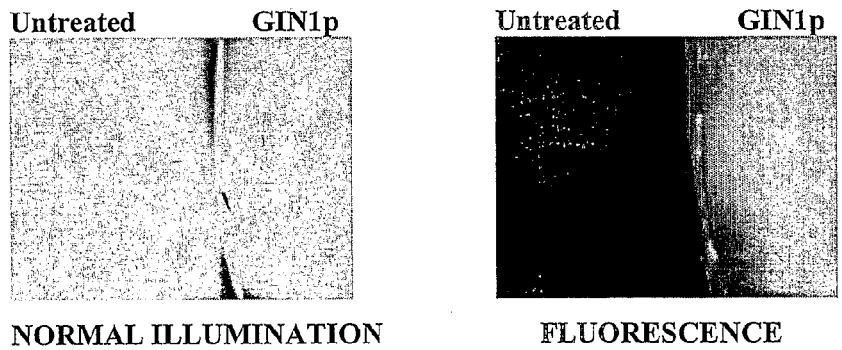
(b)
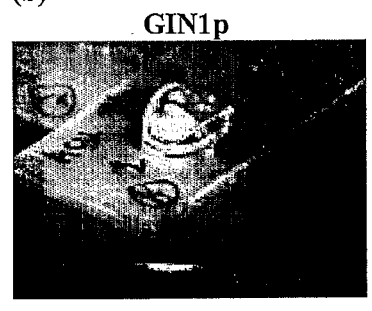

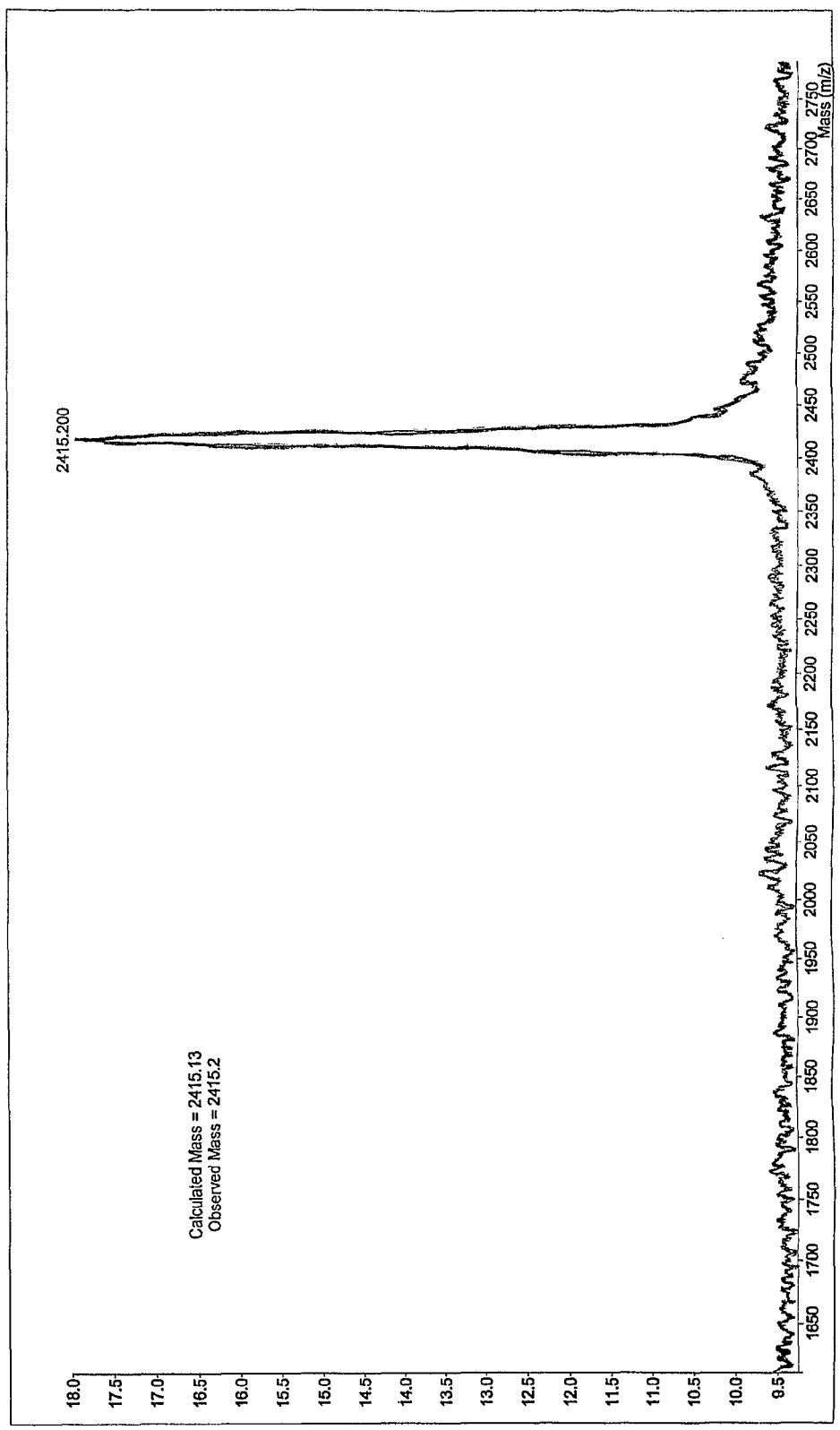
Figure: 10

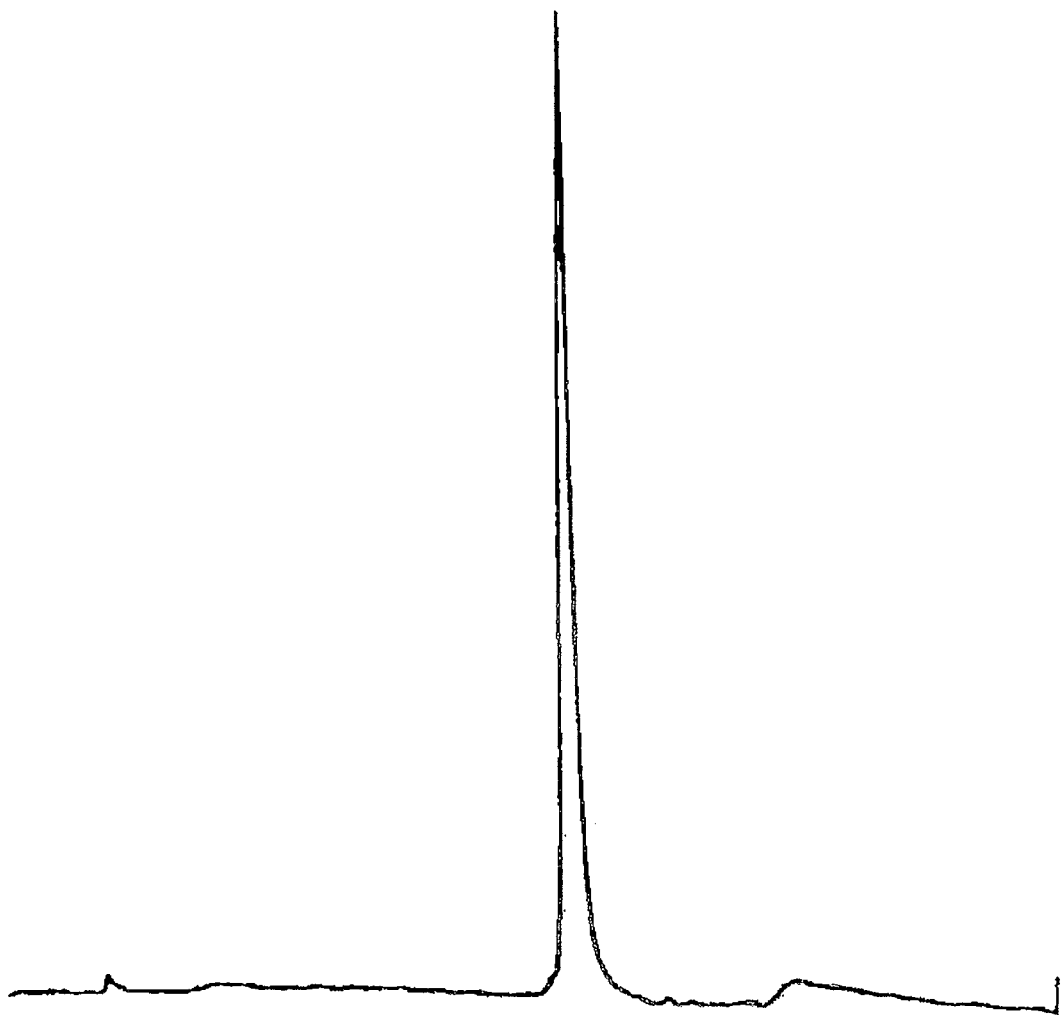
Figure: 11

TREATMENT OF BACTERIAL INFECTIONS

This application is the National Phase of International Application PCT/GB2005/000769, filed Feb. 28, 2005, which designated the U.S. and that International Application was published under PCT Article 21(2) in English. This application also includes a claim of priority under 35 U.S.C. §119(a) and §365(b) to British patent application No. GB0404374.1, filed Feb. 27, 2004.

The present invention relates to polypeptides, derivatives or analogues thereof, with antibacterial activity, and to nucleic acids encoding the same. The invention further provides the use of such polypeptides, derivatives, analogues or nucleic acids as medicaments, and also in methods of treatment. The invention further extends to objects coated with the polypeptides.

Antimicrobial peptides are a key component of the innate immune system, generally containing 20-40 amino acids, having a net positive charge, and with the majority having been identified so far in non-mammalian species. The latter limits their usefulness as therapeutics in humans or mammals, both due to difficulties in commercial production of such large peptides, and due to the risk of adverse effects of these peptides due to their non-human origin. By 2003, of the around 800 sequences listed in the Trieste international antimicrobial peptide database (http://www.bbcm.units.it/~tossi/amsdb.html), only 33 were of human origin, and of these only 3 are less than 20 amino acids in length. Some short synthetic antimicrobial peptides have also been developed. However, these have the disadvantage of associated risks of antigenic or toxic effects due to their non-human origin.

Such peptides have been characterised into six groups (Bradshaw, J. P., Biodrugs, 2003: 17: 235-240), with the following three classes being most studied (Bowman H. G., Journal of Internal Medicine, 2003: 254:197-215):

(i) Linear peptides lacking cysteines and often with an α-helical amphipathic structure in solution, for example, Human LL-37 (SEQ ID No. 19):—LLGDF-FRKSKEKIGKEFKRI VQRIKDFLRN LVPRTES;

(ii) Peptides with 3 disulphide bonds, giving peptides with a flat dimeric beta-sheet, for example, Human α-defensin:—HNP-1 (SEQ ID No. 20)

```
ACYCRIPACI AGERRYGTCI YQGRLWAFCC
```

(iii) Peptides with unusual bias in certain amino acids such as proline, arginine, tryptophan or histidine, for example, Pig PR-39 (SEQ ID No. 21):—RRRPRPPYLP RPRPPPFFPP RLPPRIPPGF PPRFPPRFP; or cow indolicidin (SEQ ID No. 22):—ILPWKWPWWP WRR.

Many antimicrobial peptides have the capacity to lyse bacteria. However, it is unclear whether cell lysis is the mechanism responsible for such antimicrobial effects (Bowman supra). In addition, many antibacterial peptides have a net positive charge, and have an element of amphipathicity with a hinge that could help the peptide to flip into a bacterial membrane. However, both of these features are common to many peptides, including, for example, polypeptide hormones (Bowman supra). Hence, at present, the mechanism by which antimicrobial peptides impart their antimicrobial function is not fully understood. Although some have been found to exert antiviral action also, this is considered to be a minor side effect of any membrane disrupting action of these peptides (Bowman supra).

A number of antibacterial peptides that have been described in the scientific literature have strong cationic character, and often consist of arginine and lysine residues. However, not all peptides containing arginine and lysine have antimicrobial activity. For example, Azuma et al. (Peptides, 21: 327-330 (2000)) reported that a 30-mer (30 amino acids in length) monomeric peptide consisting of apoE$_{133-162}$ (LRVR-LASHLRKLRKRLLRDADDLQKRLAVY; SEQ ID No. 47) had antimicrobial activity, which was comparable with that of the antibiotic gentamicin. However, the authors found that substituting individual arginines at positions 136, 142, 147 and 150 of the peptide diminished antibacterial activity, with residues at positions 142 and 147 appearing to be the most crucial. In addition, as Azuma designed shorter peptides approaching this region, the antibacterial activity declined. For example, Azuma's peptide apoE$_{134-155}$ (18 amino acids in length) had no activity at all despite containing arginines both at positions 142 and 147. Similarly, Azuma demonstrated that the peptide apoE$_{134-159}$ (22 amino acids in length) had very low antibacterial activity, and the peptide apoE$_{134-159}$ (26 amino acids in length) had greatly reduced antibacterial activity. Hence, Azuma demonstrated that reducing the length of the peptide from 30 amino acids down to 26 amino acids, and 22 amino acids, respectively, resulted in a considerable reduction in antibacterial efficacy of the peptide. They also found that reducing the peptide length still further down to 18 amino acids resulted in total loss of antibacterial efficacy. Finally, Azuma et al. only investigated the antibacterial activity of the apoE derived peptides, and did not evaluate any other antimicrobial effects.

Therefore, it appears that Azuma et. al. had no means to harness the potential antibacterial activity of their apoE$_{133-162}$ peptide, and demonstrated that simply constructing a peptide, which was cationic, did not necessarily guarantee that it would exhibit antibacterial efficacy. Hence, the mechanism by which Azuma's peptide imparted it's antibacterial nature was not at all clear.

One of the inventors of the present invention has previously established that certain polypeptides have antiviral activity. The results of his research are described in PCT/GB2004/005438 and PCT/GB2004/005360. These antiviral polypeptides comprise tandem repeats, and variants thereof, of the peptides: apoE$_{141-149}$ (LRKLRKRLL—SEQ ID No. 1) and apoB$_{3359-3367}$ (RLTRKRGLK—SEQ ID No. 2) as-well-as repeats of closely related modifications of SEQ ID No. 1 or SEQ ID No. 2. These peptides are either derived from or comprise the LDL receptor/HSPG receptor binding region of these apolipoproteins E and B. While the inventors do not wish to be bound by any hypothesis, they consider it likely that these antiviral polypeptides exert their antiviral actions by a number of mechanisms, with those affecting viral attachment being particularly favoured. The inventors suggest that dimerisation of peptides derived from the LDL receptor/HSPG receptor binding region of these apolipoproteins (as a tandem repeat or variants thereof) is important for an antiviral effect.

Despite the fact that antiviral agents are unrelated to antibacterial agents due to their different modes of action on viruses and bacteria, respectively, the inventors decided to investigate whether polypeptides, based on the antiviral peptides discussed above, had any anti-bacterial properties. To this end, they have investigated whether lytic or other effects exhibited by such peptides are possible with bacteria, even though these seemed not to occur when investigating viruses.

Specifically, the inventors wondered whether construction of repeat (e.g. tandom repeats) of peptides derived from the LDL receptor/HSPG receptor binding region of these apolipoproteins may have antibacterial effects. In particular they wondered if repeats of the apoE$_{141-149}$ region might unexpectedly allow the antibacterial properties of apoE$_{133-162}$ (disclosed in Azuma et. al. supra) to be recaptured within a much shorter polypeptide. To their surprise, they found that polypeptides, as defined below, exhibit antibacterial activity.

According to a first aspect of the present invention, there is provided use of a polypeptide, or a derivative or analogue thereof, comprising repeats of a peptide derived from a Heparan Sulphate Proteoglycan (HSPG) receptor binding region of an apolipoprotein for the manufacture of a medicament for the treatment of a bacterial infection or contamination.

By the term "derivative or analogue thereof", we mean a polypeptide within which amino acids residues are replaced by residues (whether natural amino acids, non-natural amino acids or amino acid mimics) with similar side chains or peptide backbone properties. Additionally, either one or both terminals of such peptides may be protected by N and C-terminal protecting groups, for example, groups with similar properties to acetyl or amide groups. It will be appreciated that the amino acid sequenced may be varied, truncated or modified once the final polypeptide is formed or during the development of the repeated peptides (e.g. the 9-mer).

The polypeptide of the invention comprises at least two repeats of a peptide derived from an HSPG receptor binding region of an apolipoprotein. It will be appreciated that the polypeptide may comprise repeats of the same peptide (i.e a homodimer or polymer of the same peptide). Alternatively the polypeptide may comprise a repeat of two or more related peptides (i.e. a heterodimer or a polymer comprising two or more peptide types of peptide monomer). If the polypeptide comprises different peptides, it will be appreciated that such peptides will share the characteristics that they are, or are derived form, an HSPG receptor binding region of an apolipoprotein. Polypeptides according to the invention should comprise dimers or polymers of such peptides linked N terminal to C terminal in a fashion that would be known to one skilled in the art as a tandem repeat. Accordingly, unless the context dictates otherwise, when we refer to "tandem repeats" herein we mean a repeat of peptides that are, or are derived from, an HSPG receptor binding region of an apolipoprotein. Such tandem repeats may be homodimers (or polymers of a single peptide) or may comprise a heterodimer (or polymer of related peptides) as discussed above.

The term "peptides derived from" as used herein is intended to describe or include peptides from the HSPG receptor binding region of an apolipoprotein that have been modified. Suitable modification may include amino acid substitution, addition or deletion. The derivative peptide or modified peptide is arranged as a tandem repeat in accordance with the first aspect of the invention. Surprisingly, polypeptides, derivatives or analogues thereof according to the first aspect of the invention have been shown to exhibit antibacterial activity.

When the term "a truncation thereof" is used herein, we mean that the polypeptide according to the invention or the constituent peptide is reduced in size by removal or deletion of amino acids. The reduction of amino acids may be by removal of residues from the C or N terminal of the polypeptide, or may be by deletion of one or more amino acids from within the constituent peptides.

The inventors have found that polypeptides as defined above have antiviral activity. To the inventors' surprise, when the polypeptides according to the first aspect were tested on bacteria, they also showed antibacterial efficacy, as shown in the Examples. Hence, it is the inventors' belief that they have therefore shown a new medical indication for these polypeptides.

When the polypeptide is used to treat bacterial infections it may be administered to a subject. When that subject is a human it is preferred that the polypeptide is based on repeats derived from human apolipoproteins.

The medicament may be used for the treatment of a variety of bacterial infections, including: microbial keratitis; conjunctivitis; bronchopulmonary infections, for example, pneumonia; urinary tract infections, for example, cystitis, pyelonephritis; ear, nose, and throat infections, for example, otitis media, sinusitis, laryngitis, diphtheria; skin infections including cellulitis, impetigo, wound infections, botulism, gonorrhoea; Septicaemia; peptic and duodenal ulcer; gastritis; *Campylobacter* infections; *Proteus mirabilis* infections; meningitis; osteomyelitis; and Salmonellosis.

In general, antiviral agents, such as acyclovir, ribavirin, or enfuvirtide (T-20), are rarely useful against bacterial infections due to their completely different modes of action. Similarly, antibacterial agents, such as antibiotics, are rarely useful against viral infections. Accordingly, the inventors were very surprised that the polypeptides according to the first aspect showed both antiviral and antibacterial efficacy, as this was completely unexpected.

The inventors have found that some of the specific polypeptides described herein have antibacterial activity only. However, the majority of the polypeptides according to the invention were surprisingly active as both antibacterial agents and antiviral agents. Hence, it is most preferred that the polypeptides according to the first aspect exhibit both antibacterial activity and, in addition, antiviral activity. It will be apparent that this dual activity exhibited by the polypeptides is most advantageous, as they may be used to combat or treat both viral and bacterial infections, preferably, simultaneously. They will therefore have great utility, for example, for use in hospitals, surgical theatres, and for domestic use in the home.

The polypeptides according to the first aspect of the invention may comprise repeats of peptides derived from a Heparan Sulphate Proteoglycan (HSPG) receptor binding region of apolipoprotein B or apolipoprotein E. It is preferred that the polypeptide according to the first aspect of the invention comprises a tandem repeat (as defined above) of peptides derived from an apolipoprotein B LDL receptor binding domain cluster B, as defined by Law and Scott (J. Lipid Res. 1990, 31:1109-20), or alternatively, from an apolipoprotein E LDL receptor binding domain cluster B (J. Lipid Res. 1995, 36:1905-1918). The apolipoprotein B LDL receptor binding domain cluster B may be located within an HSPG receptor binding region of apolipoprotein B, and the apolipoprotein E LDL receptor binding domain cluster B of apolipoprotein E may be located within an HSPG binding domain of apolipoprotein E.

The inventors conducted exhaustive experiments to assess the antibacterial activity of peptides from apolipoproteins and derivatives thereof. Peptides and derivatives from ApoE and ApoB were a particular focus. The inventors found that the apoE$_{141-149}$ monomeric sequence (SEQ ID No. 1) and the apoB$_{3359-3367}$ (SEQ ID No. 2) and the modified apoB$_{3359-3367}$ (SEQ ID No. 96) had no detectable antibacterial activity. In addition, to the inventor's surprise they found that a large number of other related peptides had little or no antibacterial effect (see Example 1, Tables 5 and 6). However, surprisingly, the inventors found that repeats of such peptides (i.e. polypeptides in accordance with the first aspect of the present invention), do exhibit antibacterial activity. Example 1 illustrates the efficacy of the polypeptides according to the invention compared to apoE$_{141-149}$ and apoB$_{3359-3367}$ (i.e. non-tandem repeats) and other peptides derived from apolipoproteins.

While the inventors do not wish to be bound by any hypothesis, the inventors believe that the cationic amino acid residues in the apoE$_{141-149}$ peptides (based on SEQ ID No. 1) and apoB$_{3359-3367}$ peptides (based on SEQ ID No. 2) and modified apoB$_{3359-3367}$ peptides (based on SEQ ID No. 96) when in the form of tandem repeats allows comparable anti-bacterial activity to that reported for the large Azuma peptide (apoE$_{133-162}$—referred to above). The inventors have also established that certain derivatives of these peptides also have antibacterial activity, including modifications and truncations of the peptide sequences.

The inventors carried out some detailed analysis of polypeptides with antibacterial activity and in particular those based on repeats of peptides derived from the Heparan Sulphate Proteoglycan (HSPG) receptor binding region of apolipoprotein B or apolipoprotein E. The inventors produced a sequence alignment between the amino acids of apoE$_{141-149}$ (i.e. the 9-mer of SEQ ID No. 1), aligned with the amino acids of apoB$_{3359-3367}$ (i.e. the 9-mer of SEQ ID No. 2), and also the modified form of apoB$_{3359-3367}$ (i.e. the 9-mer of SEQ ID No. 96). The sequence alignment is shown in Table 1. It will be appreciated that these three 9-mers, or derivatives thereof, are repeated in the polypeptides according to the present invention to form at least an 18-mer, which may be optionally truncated.

TABLE 1

Analysis of effective peptide sequences exhibiting antibacterial properties

| 0 | 1 | 2 | 3 | 4 | 5 | 6 | 7 | 8 | 9 |
|---|---|---|---|---|---|---|---|---|---|
| L | R | K | L | R | K | R | L | L | - |
| - | R | L | T | R | K | R | G | L | K |
| - | L | R | T | R | K | R | G | R | K | apoE (141-149) - SEQ ID No. 1
apoB (3359-3367) - SEQ ID No. 2
Modified apoB (3359-3367) - SEQ ID No. 96

Indicates residue is the same residue in apoB 3359-3367 and apoE (141-149)

In the light of this alignment data, the inventors noticed that there was a recurring (conserved) amino acid motif in each of the antibacterial polypeptides comprising tandem repeats of a peptide derived from a Heparan Sulphate Proteoglycan (HSPG) receptor binding region of apolipoprotein B (apoB$_{3359-3367}$ (SEQ ID No. 2)), or the modified apolipoprotein B (apoB$_{3359-3367}$ (SEQ ID No. 96)), or apolipoprotein E (apoE$_{141-149}$ (SEQ ID No. 1)), or a truncation thereof. This motif corresponds to a tripeptide: Arginine-Lysine-Arginine (RKR), which is found at amino acid residues designated: 4,5,6 of SEQ ID. No. 1, and SEQ ID No. 96, and SEQ ID No. 2. The inventors noticed that all of the polypeptides according to the invention exhibiting antibacterial activity comprise these RKR motifs.

Therefore, it is especially preferred that the polypeptide according to the invention comprises at least two RKR motifs (i.e. the polypeptide comprises a tandem repeat of peptides comprising RKR motifs).

It will be appreciated that polypeptides according to the present invention comprise at least two or more RKR motifs (i.e. one RKR motif per repeat). In situations where the polypeptide comprises a trimer (3×) repeat, or tetramer (4×) repeat, or an even greater number of repeat, the polypeptide preferably comprises at least three, or at least four RKR motifs, respectively.

In one embodiment of the invention, the polypeptide according to the first aspect may preferably have formula I:

{abcRKRxyz}+{a'b'c'RKRx'y'z'} wherein a,b,c,a',b',c',x,y,z,x',y',z' are amino acid residues, and wherein the polypeptide comprise peptide abcRKRxyz and peptide a'b'c'RKRx'y'z' which are repeats of SEQ ID No. 1, SEQ ID No. 2, or SEQ ID No. 96 and derivatives thereof. Such derivatives comprise SEQ ID No. 1, SEQ ID No. 2, or SEQ ID No. 96 wherein at least one amino acid residue of that peptide, other than the RKR motifs, may be replaced by an Arginine (R), Tyrosine (Y), Methionine (M), Isoleucine (I), Phenylalanine (F), Tryptophan (W), or a derivative thereof. The peptide may also comprise a Histidine (H) substitution, and preferably, consists of only one H substitution.

Suitably, one or more, more suitably, two or more, and even more suitably, three or more amino acid residues may be replaced by an Arginine (R), Tyrosine (Y), Methionine (M), Isoleucine (I), Phenylalanine (F), Tryptophan (W), or derivative thereof. Preferably, four or more, more preferably, five or more, and even more preferably, six or more amino acid residues may be replaced by these amino acids or a derivative thereof. Preferably, the replaced or substituted residue is the first, second, third, seventh, eighth, ninth, tenth, eleventh, twelfth, sixteenth, seventeenth or eighteenth residue of the peptide defined by formula I. Most preferred amino acid substitutions are with a Phenylalanine (F) residue or a Tryptophan (W) residue, or a derivative thereof.

The polypeptide according to the invention may comprise 18 amino acids (or derivatives thereof), and thereby correspond to the sequence defined by formula I with or without the substitutions discussed above. In this case, amino acid position 1 corresponds to a; position 2 corresponds to b; position 3 corresponds to c, position 4 corresponds to the amino acid R (of the RKR motif), and so on.

However, the inventors have surprisingly found that truncated polypeptides based on formula I also have efficacy as antibacterial agents. Accordingly, preferred polypeptides or derivatives thereof may have less than 18 amino acids. For instance, some polypeptides according to the first aspect of the invention may be 17, 16, 15, 14, 13, 12, 11, 10 or less amino acids in length. Deletions are preferably made at positions 1, 2, 8, 9, 10, 11, 17 and/or 18 of the polypeptide defined by formula I.

The inventor has also surprisingly found that polypeptides based on formula I but having additional amino acid residues, also have efficacy as antibacterial agents. Accordingly, preferred polypeptides or derivatives thereof may have greater than 18 amino acids. For instance, some polypeptides according to the first aspect of the invention may be 19, 20, 21, 22, 23, 24, 25, 26, 27, 28, 29 or more amino acids in length. Additions may be made to the N or C-terminal or in the core of the polypeptide. Additions may be made either before residue 'a' (i.e. at the N-terminal end of the polypeptide), or before "a" (i.e. in the core of the polypeptide), as defined in formula I. Additions may be made either after residue 'z' (i.e. in the core of the peptide) or after "z" (at the C-terminal end of the peptide), as defined in formula I.

However, the addition is preferably made at position 0, 1, 2, 8, 9, 10, 11, 17 and/or 18 of the peptide defined by formula I.

Most preferably, additions are made before position 0 of the peptide, i.e. amino acids are added to the N-terminal before the first amino acid at residue 'a' defined by formula I.

The polypeptide according to formula I may preferably comprise the following amino acids:

a & a'=is independently selected from Arginine (R); Tyrosine (Y); Methionine (M); Isoleucine (I); Phenylalanine (F); Tryptophan (W); Leucine (L); Lysine (K); Histidine (H); or is deleted;

b & b'=is independently selected from Arginine (R); Tyrosine (Y); Methionine (M); Isoleucine (I); Phenylalanine (F); Tryptophan (W); Leucine (L); Lysine (K); or is deleted;

c & c'=is independently selected from Arginine (R); Tyrosine (Y); Methionine (M); Isoleucine (I); Phenylalanine (F); Tryptophan (W); Leucine (L); Lysine (K); Histidine (H); or Threonine (T); or is deleted;

x & x'=is independently selected from Arginine (R); Tyrosine (Y); Methionine (M); Isoleucine (I); Phenylalanine (F); Tryptophan (W); Leucine (L); Lysine (K); Histidine (H); or Glycine (G); or is deleted;

y & y'=is independently selected from Arginine (R); Tyrosine (Y); Methionine (M); Isoleucine (I); Phenylalanine (F); Tryptophan (W); Leucine (L); Lysine (K); Histidine (H); or is deleted;

z & z'=is independently selected from Arginine (R); Tyrosine (Y); Methionine (M); Isoleucine (I); Phenylalanine (F); Tryptophan (W); Leucine (L); Lysine (K); Histidine (H); or is deleted.

The polypeptide of formula I may comprise at least one additional amino acid, which may be independently selected from Arginine (R); Tyrosine (Y); Methionine (M); Isoleucine (I); Phenylalanine (F); Tryptophan (W); Leucine (L); Lysine (K); Histidine (H). Preferably, the additional amino acid is added before the amino acid at position 'a' in the peptide of formula I, i.e. to the N-terminal.

Hence, it will be appreciated that the polypeptide according to the invention may comprise an 18-mer of {abcRKRxyz} and {a'b'c'RKRx'y'z'}, in which abc, a'b'c', xyz and x'y'z' are defined as above, or a truncation thereof. It will be appreciated that, for example, a may be different to a', and b may be different to b', and c may be different to c', and so on.

The polypeptide according to the first aspect may also preferably have formula II:

{abcRKRxyz}+{abcRKRxyz} wherein a=is independently selected from Arginine (R); Tyrosine (Y); Methionine (M); Isoleucine (I); Phenylalanine (F); Tryptophan (W); Leucine (L); Lysine (K); Histidine (H); or is deleted;

b=is independently selected from Arginine (R); Tyrosine (Y); Methionine (M); Isoleucine (I); Phenylalanine (F); Tryptophan (W); Leucine (L); Lysine (K); or is deleted;

c=is independently selected from Arginine (R); Tyrosine (Y); Methionine (M); Isoleucine (I); Phenylalanine (F); Tryptophan (W); Leucine (L); Lysine (K); Histidine (H); or Threonine (T); or is deleted;

x=is independently selected from Arginine (R); Tyrosine (Y); Methionine (M); Isoleucine (I); Phenylalanine (F); Tryptophan (W); Leucine (L); Lysine (K); Histidine (H); or Glycine (G); or is deleted;

y=is independently selected from Arginine (R); Tyrosine (Y); Methionine (M); Isoleucine (I); Phenylalanine (F); Tryptophan (W); Leucine (L); Lysine (K); Histidine (H); or is deleted;

z=is independently selected from Arginine (R); Tyrosine (Y); Methionine (M); Isoleucine (I); Phenylalanine (F); Tryptophan (W); Leucine (L); Lysine (K); Histidine (H); or is deleted.

As with the polypeptide of formula I, the polypeptide of formula II may comprise at least one additional an amino acid, which may be independently selected from Arginine (R); Tyrosine (Y); Methionine (M); Isoleucine (I); Phenylalanine (F); Tryptophan (W); Leucine (L); Lysine (K); Histidine (H). Preferably, the additional amino acid is added before the amino acid at position 'a' in the peptide of formula II, i.e. to the N-terminal.

Hence, it will be appreciated that the polypeptide according to the invention comprises an 18-mer of {abcRKRxyz} and {abcRKRxyz}, in which abc and xyz are defined as above, or a truncation thereof.

The polypeptide defined by formula II preferably comprises the following amino acids:

a=is independently selected from Arginine (R); Tyrosine (Y); Methionine (M); Isoleucine (I); Phenylalanine (F); Tryptophan (W); or is deleted;

b=is independently selected from Arginine (R); Tyrosine (Y); Methionine (M); Isoleucine (I); Phenylalanine (F); Tryptophan (W); or is deleted;

c=is independently selected from Phenylalanine (F); or Tryptophan (W); or is deleted;

x=is independently selected from Phenylalanine (F); Tryptophan (W); or is deleted;

y=is independently selected from Phenylalanine (F); Tryptophan (W); or is deleted;

z=is independently selected from Arginine (R); Tyrosine (Y); Methionine (M); Isoleucine (I); Phenylalanine (F); Tryptophan (W); or is deleted.

These preferred polypeptides may comprise at least one additional amino acid, which may be either Phenylalanine (F) or Tryptophan (W) or Leucine (L). Preferably, the additional amino acid is added before the amino acid at position 'a' in the polypeptide of formula II i.e. to the N-terminal.

The inventors have also appreciated that polypeptides may be employed according to the invention that comprise more than just a tandem dimer (2×) repeat of a peptide derived from a Heparan Sulphate Proteoglycan (HSPG) receptor binding region of apolipoprotein B or apolipoprotein E, or a truncation thereof. For example, polypeptides comprising a trimer (3×) repeat, or tetramer (4×) repeat, or an even greater number of repeats of a peptide derived from a Heparan Sulphate Proteoglycan (HSPG) receptor binding region of apolipoprotein B or apolipoprotein E may be employed as useful antibacterial agents.

Accordingly, it is preferred that the polypeptide may have formula III:—

{abcRKRxyz}$^n$ wherein a, b, c, x, y, and z are as defined above with reference to formula I or II, and wherein n is equal to 2, 3, 4 or 5, or more.

Other preferred polypeptides may comprise repeats of the 18-mer peptide (or truncation thereof) defined by formula I (e.g. repeats of a heterodimer of the 9-mers comprising the peptide of formula I).

Polypeptides, and derivatives thereof, according to the invention preferably have an efficacy for inhibiting bacterial growth such that their $IC_{50}$ value is about 40 µM or less. It is preferred that the $IC_{50}$ value is about 30 µM or less, more preferably, about 20 µM or less, and most preferred about 10 µM or less. The skilled technician will appreciate how $IC_{50}$ values may be calculated.

It is most preferred that the polypeptide according to the first aspect may comprise a repeat of apoE$_{141-149}$ (SEQ ID NO. 1), or derivatives and truncations thereof.

Hence, in a second aspect, there is provided use of a polypeptide, derivative or analogue thereof comprising a repeat of the peptide apoE$_{141-149}$ (SEQ ID NO. 1) and truncations thereof, or a repeat of variants of the peptide apoE$_{141-149}$ in which at least one Leucine (L) residue is replaced by Tryptophan (W), Arginine (R), Lysine (K), Tyrosine (Y) or Phenylalanine (F), for the manufacture of a medicament for the treatment of a bacterial infection.

By "a repeat of the peptide apoE$_{141-149}$" we mean a polypeptide comprising a repeat of the peptide sequence: LRKLRKRLL (SEQ ID No 1), i.e. a 9-mer. The polypeptide preferably comprises the amino acid sequence: LRKLRKRLLLRKLRKRLL (SEQ ID NO. 6), i.e. an 18-mer which is a tandem repeat dimer of SEQ ID No. 1. SEQ ID No. 6 is also referred to herein as GIN 1 or GIN1p (wherein p signifies N terminal protection (e.g. by an acetyl group), and C terminal protection (e.g. by an amide group). GIN 1p is also referred to herein as MU 10.

By "a truncation thereof", we mean that the repeat (e.g. the 18-mer of SEQ ID No. 6) is reduced in size by removal of amino acids. The reduction of amino acids may be by removal of residues from the C- and/or N-terminal, or may be by deletion of one or more amino acids from within the core of the polypeptide (e.g. amino acids 2-17 of SEQ ID No. 6).

The inventor has identified that Tryptophan (W), Arginine (R), Lysine (K), Tyrosine (Y), or Phenylalanine (F) may be substituted for Leucine in apoE$_{141-149}$ tandem repeats, and that such polypeptides have surprising antibacterial activity.

It is most preferred that polypeptides according to the second aspect of the invention comprise a polypeptide, derivative or analogue thereof comprising a dimer repeat of apoE$_{141-149}$ or a truncation thereof, characterised in that at least one Leucine (L) residue of the dimer (SEQ ID No. 6) is replaced by a Tryptophan (W), or a Phenylalanine (F) residue.

As discussed in more detail below, SEQ ID No. 6 may be manipulated with a number of different substitutions and deletions to make polypeptides with antibacterial activity. It is preferred that the polypeptide according to the second aspect of the invention has at least two substitutions independently selected from: Tryptophan (W), Arginine (R), Lysine (K), Tyrosine (Y), or Phenylalanine (F) substitutions, and more preferably three or more Tryptophan (W), Arginine (R), Lysine (K), Tyrosine (Y), or Phenylalanine (F) substitutions.

In addition to one or more L substitutions with K, R, Y, F, or W, it is preferred that at least one further amino acid (preferably at least one further Leucine residue) is replaced with Arginine (R), Tyrosine (Y), Methionine (M), Isoleucine (I), Phenylalanine (F), or Tryptophan (W). It is particularly preferred that such a further substitution is F or W.

The inventor has also appreciated that polypeptides may be employed according to the invention that comprise more than just a dimer tandem repeat of ApoE$_{141-149}$ or a truncation or variant thereof. For instance, a trimer or tetramer or greater number of repeats may be employed as antibacterial agents.

The polypeptides according to the second aspect may be synthesised such that further amino acids are added thereto. For instance, one, two, three or more amino acids may be added to the C or N terminals of a peptide derived from SEQ ID No. 6. Alternatively, the polypeptide may comprise a tandem repeat of a peptide that is larger than the nine amino acids of SEQ ID No. 1. Such peptides may have amino acids added to the N terminal, C terminal and/or between the 9$^{th}$ and 10$^{th}$ amino acids of SEQ ID No. 6. It is most preferred that the amino acid is added to the C terminal and also between the 9$^{th}$ and 10$^{th}$ amino acids of SEQ ID No. 6. It will be appreciated that such peptides may then be modified as described above for polypeptides derived from SEQ ID No. 6.

The substituted polypeptide may comprise 18 amino acids (or derivatives thereof) and thereby correspond to the full length of SEQ ID No. 6. However, the inventors have surprisingly found that some selected truncated polypeptides based on SEQ ID No. 6 also have efficacy as antibacterial agents. Accordingly, preferred polypeptides or derivatives thereof may have less than 18 amino acids. For instance, some polypeptides according to the second aspect of the invention may be 17, 16, 15, 14, 13, 12, 11, 10 or less amino acids in length.

It will be appreciated that modified forms of W or Y or R or K or F may be substituted into the tandem repeat of apoE$_{141-149}$ with a number of amino acid variants that may be known to those skilled in the art. Such polypeptides will still have antibacterial activity provided that the modification does not significantly alter its chemical characteristics. For instance, hydrogens on the side chain amines of R or K may be replaced with methylene groups (—NH$_2$→—NH(Me) or —N(Me)$_2$).

Other preferred polypeptides according to the second aspect of the invention (comprising tandem repeats of peptides derived from apoE$_{141-149}$) may comprise one of the following amino acid sequences:—

(a) WRKWRKRWWWRKWRKRWW (SEQ ID No. 7). This polypeptide corresponds to a full length tandem dimer repeat of apoE$_{141-149}$ (SEQ ID NO. 6) with all Leucines substituted for Tryptophan residues. This polypeptide is designated GIN 7 or MU 4 when referred to herein.

(b) WRKWRKRWRKWRKR (SEQ ID No. 8). This polypeptide corresponds to the full length tandem dimer repeat of apoE$_{141-149}$ (SEQ ID NO. 6) with all Leucines substituted for Tryptophan residues and truncated by the excision of amino acids 9, 10, 17 and 18, i.e. is a 14-mer. This polypeptide is designated GIN 32 when referred to herein.

(c) WRKWRKRWWLRKLRKRLL (SEQ ID No. 9). This polypeptide corresponds to the full length tandem dimer repeat of apoE$_{141-149}$ (SEQ ID NO. 6) with a subset of Leucines substituted for Tryptophan residues, i.e. is an 18-mer. This polypeptide is designated GIN 34 when referred to herein.

(d) YRKYRKRYYYRKYRKRYY (SEQ ID No. 10). This polypeptide corresponds to the full length tandem dimer repeat of apoE$_{141-149}$ (SEQ ID NO. 6) with all Leucines substituted for tyrosine residues, i.e. is an 18-mer. This polypeptide is designated GIN 41 when referred to herein.

(e) LRKLRKRLRKLRKR (SEQ ID No. 11). This polypeptide corresponds to the full length tandem dimer repeat of apoE$_{141-149}$ (SEQ ID NO. 6) truncated by the excision of amino acids 9, 10, 17 and 18, i.e. is an 14-mer. This polypeptide is designated GIN 8 when referred to herein.

(f) LRKRLLLRKLRKRLL (SEQ ID No. 3). This polypeptide corresponds to the full length tandem dimer repeat of apoE$_{141-149}$ (SEQ ID NO. 6) truncated by the excision of amino acids 1, 2 and 3, i.e. is a 15-mer. This polypeptide is designated GIN 2 when referred to herein.

(g) FRKFRKRFFFRKFRKRFF (SEQ ID No. 48). This polypeptide is designated MU 7 when referred to herein.

(h) WRKWRKRWWRKWRKRWW (SEQ ID NO. 63). This polypeptide corresponds to SEQ ID No. 7 with the W residue at position 9 deleted. This polypeptide is designated MU 58 when referred to herein.

(i) WRKWRKRWRKWRKRW (SEQ ID NO. 64). This polypeptide corresponds to SEQ ID No. 7 with the W residues at position 9, 10 and 18 deleted. This polypeptide is designated MU 59 when referred to herein.

(j) WRKWRKRWWFRKWRKRWW (SEQ ID NO. 65). This polypeptide corresponds to SEQ ID No. 7 with the W residue at position 10 substituted with an F. This polypeptide is designated MU 60 when referred to herein.
(k) WRKWRKRFFWRKWRKRFF (SEQ ID NO. 66). This polypeptide corresponds to SEQ ID No. 7 with the W residues at positions 9, 10, 17 and 18 substituted with F residues. This polypeptide is designated MU 61 when referred to herein.
(l) WRKRWWRWRKRWWR (SEQ ID NO. 67). This polypeptide is designated MU 81 when referred to herein.
(m) LRKLRKRLLRLRKLRKRLLR (SEQ ID NO. 68). This polypeptide is designated MU 82 when referred to herein.
(n) WRKWRKRWWRWRKWRKRWWR (SEQ ID NO. 69). This polypeptide is designated MU 83 when referred to herein.
(O) LRKLRKRLLWRKWRKRWW (SEQ ID NO. 70). This polypeptide corresponds to SEQ ID No. 6 with the L residues at positions 10, 13, 17 and 18 substituted with W residues. This polypeptide is designated MU 111 when referred to herein.
(p) LRKLRKRLLLRKLRKRWW (SEQ ID NO. 71). This polypeptide corresponds to SEQ ID No. 6 with the L residues at positions 17 and 18 substituted with W residues. This polypeptide is designated MU 112 when referred to herein.
(q) LRKLRKRLLWRKWRKRLL (SEQ ID NO. 72). This polypeptide corresponds to SEQ ID No. 6 with the L residues at positions 10 and 13 substituted with W residues. This polypeptide is designated MU 113 when referred to herein.
(r) WRKWRKRLLLRKLRKRLL (SEQ ID NO. 73). This polypeptide corresponds to SEQ ID No. 6 with the L residues at positions 1 and 4 substituted with W residues. This polypeptide is designated MU 114 when referred to herein.
(s) WRKLRKRLLLRKLRKRLL (SEQ ID NO. 74). This polypeptide corresponds to SEQ ID No. 6 with the L residue at position 1 substituted with W residues. This polypeptide is designated MU 115 when referred to herein.
(t) WRKWRKFFFRKWRKRWW (SEQ ID NO. 75). This polypeptide corresponds to SEQ ID No. 7 with the W residues at positions 8, 9 and 10 substituted with F residues and the R residue at position 7 deleted. This polypeptide is designated MU 116 when referred to herein.
(u) WRKWRKRWWFRKFRKRFF (SEQ ID NO. 76). This polypeptide corresponds to SEQ ID No. 7 with the W residues at positions 10, 13, 17 and 18 substituted with F residues. This polypeptide is designated MU 117 when referred to herein.

Some of the most preferred polypeptides according to the first aspect of the invention comprise repeats of peptides derived from an HSPG receptor binding region of apolipoprotein B, or a variant or truncation thereof.

Hence, in a third aspect, there is provided use of a polypeptide, or a derivative or analogue thereof, comprising repeats of a peptide derived from an HSPG receptor binding region of apolipoprotein B, for the manufacture of a medicament for the treatment of a bacterial infection or contamination.

Preferably, the polypeptide, derivative or analogue thereof comprises a repeat which is derived from an apolipoprotein B LDL receptor binding domain cluster B. Preferably, the polypeptide, derivative or analogue thereof comprises a repeat of the peptide apoB$_{3359-3367}$ (SEQ ID No. 2) or a truncation or variant thereof.

The polypeptide according to the third aspect of the invention may be a tandem dimer repeat of apoB$_{3359-3367}$ (SEQ ID No. 2) with the amino acid sequence: RLTRKRGLKRLTRKRGLK, i.e. an 18-mer (SEQ ID No. 12).

Peptides according to the third aspect of the invention may also be truncated as defined herein. The reduction of amino acids may be by removal of residues from the C- and/or N-terminal, or may be by deletion of one or more amino acids from within the core of the peptide (i.e. amino acids 2-17 of SEQ ID No. 12).

It is preferred that polypeptides according to the third aspect comprise at least two RKR motifs, or more if the polypeptide is a trimer, or tetramer, and so on.

Preferred polypeptides according to the third aspect comprises the tandem dimer repeat of the peptide apoB$_{3359-3367}$ (i.e the polypeptide of SEQ ID No. 12) or a truncation thereof, characterised in that at least one amino acid residue, other than the RKR motifs, has been replaced by a Glycine (G), Threonine (T), Histidine (H), Tryptophan (W), Arginine (R) or Leucine (L) residue or derivatives thereof.

Suitably, one or more, more suitably, two or more, and even more suitably, three or more amino acid residues may be replaced by a Glycine (G), Threonine (T), Histidine (H), Tryptophan (W), Arginine (R) or Leucine (L) residue or derivative thereof. Preferably, four or more, more preferably, five or more, and even more preferably, six or more amino acid residues may be replaced by these amino acids or derivative thereof. Preferably, the replaced or substituted residue is the first, second, third, seventh, eighth, ninth, tenth, eleventh, twelfth, sixteenth, seventeenth or eighteenth residue of SEQ ID No. 12.

Preferably, the polypeptide according to the third aspect comprises the polypeptide of SEQ ID No. 12 or a truncation thereof, characterised in that at least one amino acid residue has been replaced by a Tryptophan (W), Arginine (R) or Leucine (L) residue or derivative thereof.

Suitably, one or more, more suitably, two or more, and even more suitably, three or more amino acid residues may be replaced by a Tryptophan (W), Arginine (R) or Leucine (L) residue or derivative thereof. Preferably, four or more, more preferably, five or more, and even more preferably, six or more amino acid residues may be replaced by a Tryptophan (W), Arginine (R) or Leucine (L) residue or derivative thereof. Preferably, the replaced or substituted residue is the first, second, third, seventh, eighth, and/or ninth residue of the repeated amino acid sequence of apoB$_{335-3367}$, or combinations thereof.

The polypeptide according to the invention may comprise 18 amino acids (or derivatives thereof) and thereby correspond to the full length of SEQ ID No. 12 with or without the substitutions discussed above. However, the inventors have surprisingly found that truncated polypeptides based on SEQ ID No. 12 also have efficacy as antibacterial agents. Accordingly, preferred polypeptides or derivatives thereof may have less than 18 amino acids. For instance, some polypeptides according to the third aspect of the invention may be 17, 16, 15, 14, 13, 12, 11, 10 or less amino acids in length. Deletions are preferably made at positions 1, 2, 8, 9, 10, 11, 17 and/or 18 of SEQ ID No. 12.

In a preferred embodiment, the polypeptide according to the third aspect may preferably have formula IV:

{abcRKRxyz}+{a'b'c'RKRx'y'z'} wherein
a & a'=is independently selected from a positively charged residue, which may be selected from either Arginine (R) or Lysine (K) or Histidine (H); Leucine (L); Tryptophan (W); or is deleted;
b & b'=is independently selected from Leucine (L); Arginine (R); Lysine (K); or is deleted;
c & c'=is independently selected from Threonine (T); Tryptophan (W); or a positively charged residue, which may be selected from Arginine (R) or Lysine (K) or Histidine (H);

x & x'=is independently selected from Glycine (G); Tryptophan (W); Leucine (L); or a positively charged residue, which may be selected from Arginine (R) or Lysine (K) or Histidine (H);

y & y'=is independently selected from Leucine (L); a positively charged residue, which may be selected from Arginine (R) or Lysine (K) or Histidine (H); or is deleted;

z & z'=is independently selected from a positively charged residue, which may be selected from Arginine (R) or Lysine (K) or Histidine (H); or Leucine; or is deleted.

The polypeptide according to the third aspect may also preferably have formula V:

{abcRKRxyz}+{abcRKRxyz} wherein a=is independently selected from a positively charged residue, which may be selected from either Arginine (R) or Lysine (K) or Histidine (H); Leucine (L); Tryptophan (W); or is deleted;

b=is independently selected from Leucine (L); Arginine (R); Lysine (K); or is deleted;

c=is independently selected from Threonine (T); Tryptophan (W); or a positively charged residue, which may be selected from Arginine (R) or Lysine (K) or Histidine (H);

x=is independently selected from Glycine (G); Tryptophan (W); Leucine (L); or a positively charged residue, which may be selected from Arginine (R) or Lysine (K) or Histidine (H);

y=is independently selected from Leucine (L); a positively charged residue, which may be selected from Arginine (R) or Lysine (K) or Histidine (H); or is deleted;

z=is independently selected from a positively charged residue, which may be selected from Arginine (R) or Lysine (K) or Histidine (H); or Leucine (L); or is deleted.

The polypeptide of formula V may more preferably comprise the following amino acids:

a=is independently selected from Tryptophan (W); Arginine (R); Leucine (L); or is deleted;

b=is independently selected from Leucine (L); Arginine (R) or Lysine (K); or is deleted;

c=is independently selected from Tryptophan (W); Threonine (T); Lysine (K);

x=is independently selected from Tryptophan (W); Glycine (G); Leucine (L); Arginine (R);

y=is independently selected from Leucine (L); a positively charged residue, which may be selected from Arginine (R) or Lysine (K) or Histidine (H); or is truncated here;

z=is independently selected from a positively charged residue, which may be selected from Arginine (R) or Lysine (K) or Histidine (H); or Leucine (L); or is truncated here.

The inventors have also appreciated that polypeptides may be employed according to the invention that comprise more than just a tandem dimer repeat of apoB$_{3359\text{-}3367}$ (SEQ ID No. 12) or a variant or truncation thereof. For example, polypeptides comprising a trimer, or tetramer, or even greater number of repeats of SEQ ID No. 2 may be employed as useful antibacterial agents.

Accordingly, it is preferred that the polypeptide may preferably have formula VI:—

{abcRKRxyz}$^n$ wherein a, b, c, x, y, and z are as defined above with reference to formula IV or V, and wherein n is equal to 2, 3, 4 or 5, or more. It will be appreciated that monomer peptides {abcRKRxyz} may be identical or may vary as defined above.

Other preferred polypeptides may comprise repeats of the 18mer (or truncations thereof) defined by formula IV or V (e.g. repeats of a heterodimer of the 9mer peptides defined by formula IV).

Other preferred polypeptides according to the third aspect of the invention may comprise one of the following amino acid sequences:—

(a) RTRKRGRRTRKRGR.     (SEQ ID No. 13)
This polypeptide is designated GIN 36 when referred to herein;

(b) LRKRKRLLRKRKRL.     (SEQ ID No. 14)
This polypeptide is designated GIN 37 when referred to herein;

(c) LRKRKRLRKLRKRKRLRK. (SEQ ID No. 15)
This polypeptide is designated GIN 38 when referred to herein;

(d) WRWRKRWRKWRWRKRWRK. (SEQ ID No. 16)
This polypeptide is designated GIN 33 when referred to herein;

(e) LLRKRLKRLLLRKRLKRL. (SEQ ID NO. 80)
This polypeptide is designated MU 24 when referred to herein;

(f) RRWRKRWRKWRWRKRWRK. (SEQ ID NO. 83)
This polypeptide is designated MU 28 when referred to herein;

(g) KRWRKRWRKWRWRKRWRK. (SEQ ID NO. 84)
This polypeptide is designated MU 29 when referred to herein;

(h) LRWRKRWRKWRWRKRWRK. (SEQ ID NO. 85)
This polypeptide is designated MU 30 when referred to herein;

(i) HRWRKRWRKWRWRKRWRK. (SEQ ID NO. 86)
This polypeptide is designated MU 31 when referred to herein;

(j) RWRKRWRKWRWRKRWRK.  (SEQ ID NO. 87)
This polypeptide is designated MU 32 when referred to herein;

(k) RRWRKRWRKRRWRKRWRK. (SEQ ID NO. 88)
This polypeptide is designated MU 33 when referred to herein;

(l) LRWRKRWRKLRWRKRWRK. (SEQ ID NO. 89)
This polypeptide is designated MU 35 when referred to herein;

(m) HRWRKRWRKHRWRKRWRK. (SEQ ID NO. 90)
This polypeptide is designated MU 36 when referred to herein;

(n) RWRKRWRKRWRKRWRK.   (SEQ ID NO. 91)
This polypeptide is designated MU 37 when referred to herein;

(o) RWRKRGRKRWRKRGRK.   (SEQ ID NO. 92)
This polypeptide is designated MU 69 when referred to herein;

(p) RWRKRWRKRWRKRWRK.   (SEQ ID NO. 93)
This polypeptide is designated MU 71 when referred to herein;

(q) RKRGWKWRKRGWKW.     (SEQ ID NO. 94)
This polypeptide is designated MU 73 when referred to herein; and (r) RLTRKRGRLTRKRG.     (SEQ ID NO. 95)
This polypeptide is designated MU 74 when referred to herein;

During their development work (some of which was based on the previously identified antiviral polypeptides), the inventors further manipulated polypeptides according to the first, second and third aspects, and generated previously unknown polypeptides, and classes thereof, which also showed antibacterial activity.

Therefore, according to a fourth aspect, there is provided a polypeptide, derivative or analogue thereof comprising a repeat of the peptide apoE$_{141-149}$ (SEQ ID No. 1) or a variant or truncation thereof, characterised in that at least one Leucine (L) residue of SEQ ID No. 1 is replaced by Tyrosine (Y) or Phenylalanine (F).

The inventors also investigated the antibacterial efficacy of a number of other polypeptides that were synthesised for the work described herein. The inventors believe these polypeptides are new and according to further aspects, there are provided polypeptides, derivatives or analogues thereof, comprising the amino acid sequences of SEQ ID No. 3 (GIN 2); SEQ ID No. 4 (GIN 11); SEQ ID No. 67 (MU 81); SEQ ID No. 68 (MU 82); SEQ ID No. 80 (MU 24); SEQ ID No. 94 (MU 73) or SEQ ID No. 95 (MU 74).

These polypeptides are described in further detail in the Examples. By way of example, GIN 2 (SEQ ID No. 3) is a polypeptide corresponding to the full length tandem dimer repeat of the peptide apoE$_{114-149}$ (SEQ ID NO. 12) truncated by the excision of amino acids 1, 2 and 3, i.e. it is a 15-mer having an amino acid sequence: LRKRLLLRKLRKRLL. GIN 11 (SEQ ID No. 4) is a peptide comprising apoE$_{128-149}$ having an amino acid sequence of QSTEELRVRLASHL-RKLRKRLL.

According to still further aspects of the present invention, there is provided a polypeptide, derivative or analogue thereof comprising an amino acid sequence of SEQ ID No. 3 (GIN 2); SEQ ID No. 4 (GIN 11); SEQ ID No. 67 (MU 81); SEQ ID No. 68 (MU 82); SEQ ID No. 80 (MU 24); SEQ ID No. 94 (MU 73) or SEQ ID No. 95 (MU 74) for use as a medicament.

In addition, according to a still further aspect of the present invention, there is provided use of a polypeptide, derivative or analogue thereof comprising an amino acid sequence of SEQ ID No. 3 (GIN 2); SEQ ID No. 4 (GIN 11); SEQ ID No. 67 (MU 81); SEQ ID No. 68 (MU 82); SEQ ID No. 80 (MU 24); SEQ ID No. 94 (MU 73) or SEQ ID No. 95 (MU 74) or a truncation thereof, for the manufacture of medicament for the treatment of a bacterial infection.

According to a further embodiment, the polypeptide according to the invention may comprise a tandem repeat of apoE$_{133-162}$ or a truncation thereof. By "a tandem repeat of apoE$_{133-162}$", we mean a dimer of the peptide with the amino acid sequence: LRVRLASHLRKLRKRLLRDAD-DLQKRLAVY (SEQ ID No. 5). (i.e. the 60-mer polypeptide: LRVRLASHLRKLRKRLLRDADDLQKRLAVY LRVR-LASHLRKLRKRLLRDADDLQKRLAVY (SEQ ID No. 97). The apoE$_{133-162}$ peptide (a 30-mer) disclosed in Azuma et al. was shown to have some antibacterial activity. However, surprisingly, the inventors of the present invention have shown that a tandem repeat of Azuma's peptide has improved antibacterial efficacy, and this was totally unexpected.

In a further aspect, there is provided a polypeptide according to any previous aspect, for use as a medicament.

In a further aspect, there is provided use of a polypeptide according to any previous aspect, for the manufacture of a medicament for the treatment of a bacterial infection.

Due to their increased biological activity, polypeptides, derivatives or analogues according to the invention are of utility as antibacterial agents.

Polypeptides, derivatives or analogues according to the invention may be used in the treatment against any bacterium, or bacterial infection. The bacterium may be a gram positive or a gram negative bacterium.

For example, bacteria against which the peptides in accordance with the invention are effective may include Firmicutes, which may be Bacilli or Clostridia, for example *Clostridium botulinum*.

In a preferred embodiment, bacteria against which the polypeptides in accordance with the invention are effective may include Bacillales, preferably, *Staphylococcus*, for example, *Staphylococcus aureus*. Additional Bacillales with which the peptides according to the invention are effective include Streptococci, for example, *Streptococcus pyogenes* or *Streptococcus pneumoniae*.

Further examples of bacteria against which the polypeptides in accordance with the invention are effective may include Pseudomonadales, preferably, *Pseudomonas aeruginosa*. Further examples of bacteria against which the polypeptides in accordance with the invention are effective may include Gammaproteobacteria, which may be independently selected from a group consisting of Enterobacteriales, *Proteus*, Serratai, Pasteurellales, and Vibrionales. Preferred Enterobacteriales include *Escherichia*. Preferred *Proteus* include *Proteus mirabilis*. Preferred Serratai include *Serratia marcescens*. Preferred Pasteurellales include *Haemophilus influenzae*. Preferred Vibrionales include *Vibrio cholerae*.

Further examples of bacteria against which the polypeptides in accordance with the invention are effective may include Betaproteobacteria, including Neisseriales, for example, *Neisseria gonorrhoeae*. Further examples of bacteria against which the polypeptides in accordance with the invention are effective may include Delta/epsilon subdivided Proteobacteria, including Campylobacterales, for example *Helicobacter pylori*. Further examples of bacteria against which the polypeptides in accordance with the invention are effective may include Actinobacteria, for example *Mycobacterium tuberculosis* and *Nocardia asteroides*.

The inventors conducted experiments to determine which of the polypeptides disclosed herein exhibited antibacterial activity against the test bacteria *Staphylococcus aureus*, and *Pseudomonas aeruginosa*, and *Streptococcus pneumoniae*. The activity of polypeptides in accordance with the invention can be seen in Tables 5, 6, 7 and 8. Preferably, the polypeptides according to the invention exhibit antibacterial activity against at least one, preferably at least two, and more preferably, all of *S. aureus, P. aeruginosa*, and *S. pneumoniae*. Preferably, the polypeptides according to the invention exhibit antibacterial activity against both *S. aureus*, and *P. aeruginosa*. However, the inventors have found that GIN 7, MU 58, MU 114, MU 61, MU 60, and GIN 41 (SEQ ID No. 10) is particularly active against *Staphylococcus*, and in particular, *S. aureus*. In addition, the inventors have found that GIN1p, MU 61, MU 82, MU 113, MU 114, MU 115, GIN 34, GIN 8 (SEQ ID No. 11), GIN 2 (SEQ ID No. 3), and GIN 11 (SEQ ID No. 4) are particularly effective against Pseudomonadales, and in particular, *P. aeruginosa*. Furthermore, the inventors found that GIN 7 (MU 4—SEQ ID No. 7), GIN 34 (SEQ ID No. 9), GIN 2 (SEQ ID No. 3), and MU 37 (SEQ ID No. 91) are particularly effective (IC$_{50}$ values less than 30 μM) against *Streptococcus*, and in particular, *S. pneumoniae*.

Polypeptides, derivatives or analogues according to the invention may be used to treat bacterial infections as a monotherapy (i.e. use of the polypeptide or nucleic acid alone) or in combination with other compounds or treatments used in antibacterial therapy. For example, conventional antibiotics include amikacin, amoxicillin, aztreonam, cefazolin, cefepime, ceftazidime, ciprofloxacin, gentamicin, imipenem, linezolid, nafcillin, piperacillin, quinopristin-dalfoprisin, ticarcillin, tobramycin, and vancomycin.

Whilst the inventors do not wish to be bound by any hypothesis, they have suggested that the antibacterial mechanism of action by the polypeptides in accordance with the invention, may involve a direct damaging effect to the bacterium, either mediated through the bacterial membrane, or through targeting a site within the bacterium. It is possibly for this reason that only a surprisingly small number of peptide sequences have been found to be effective against bacteria.

It will be appreciated that the therapeutic effects of polypeptides, derivatives or analogues according to the invention may be mediated "indirectly" by agents that increase the activity of such polypeptides, derivatives or analogues.

Thus, according to a further aspect of the invention, there is provided an agent capable of increasing the biological activity of a polypeptide, derivative or analogue according to the first, second or third aspect of the invention for use as a medicament or for use for the manufacture of a medicament for treating a bacterial infection.

Agents capable of increasing the biological activity of polypeptides, derivatives or analogues according to the invention may achieve their effect by a number of means. For instance, such agents may increase the expression of such polypeptides, derivatives or analogues. Alternatively (or in addition), such agents may increase the half-life of polypeptides, derivatives or analogues according to the invention in a biological system, for example, by decreasing turnover of the polypeptides, derivatives or analogues.

Derivatives of polypeptides according to the invention may be used to treat bacterial infections. Such derivatives may increase or decrease the polypeptide's half-life in vivo. Examples of derivatives capable of increasing the half-life of polypeptides according to the invention include peptoid derivatives of the polypeptides, D-amino acid derivatives of the polypeptides, and peptide-peptoid hybrids.

Polypeptides according to the invention may be subject to degradation by a number of means (such as protease activity in biological systems). Such degradation may limit the bioavailability of the polypeptides and hence the ability of the polypeptides to achieve their biological function. There are wide ranges of well-established techniques by which derivatives that have enhanced stability in biological contexts can be designed and produced. Such polypeptide derivatives may have improved bioavailability as a result of increased resistance to protease-mediated degradation. Preferably, a derivative or analogue suitable for use according to the invention is more protease-resistant than the peptide from which it is derived.

Preferably, the polypeptide may be made more protease-resistant by protecting the N and/or C terminal. For example, the N terminal may be protected by an acetyl group, or by an alkyl or aryl group, or an alkyl-CO— or aryl-CO— group, each of which may be optionally substituted. The C terminal may be protected by an amide group or by a substituted amide group.

Protease-resistance of a polypeptide derivative and the polypeptide from which it is derived may be evaluated by means of well-known protein degradation assays. The relative values of protease resistance for the polypeptide derivative and polypeptide may then be compared.

Peptoid derivatives of the polypeptides of the invention may be readily designed from knowledge of the structure of the polypeptide according to the first, second or third aspect of the invention. Commercially available software may be used to develop peptoid derivatives according to well-established protocols.

Retropeptoids, (in which all amino acids are replaced by peptoid residues in reversed order) are also able to mimic antibacterial polypeptides derived from apolipoproteins. A retropeptoid is expected to bind in the opposite direction in the ligand-binding groove, as compared to a peptide or peptoid-peptide hybrid containing one peptoid residue. As a result, the side chains of the peptoid residues are able to point in the same direction as the side chains in the original peptide.

A further embodiment of a modified form of polypeptide according to the invention comprises D-amino acid forms of the polypeptide. The preparation of peptides using D-amino acids rather than L-amino acids greatly decreases any unwanted breakdown of such an agent by normal metabolic processes, decreasing the amounts of agent which need to be administered, along with the frequency of its administration.

The polypeptides, analogues, or derivatives of the invention represent products that may advantageously be expressed by biological cells.

The present invention also provides, in a further aspect, a nucleic acid sequence encoding a polypeptide, derivative or analogue according to the invention.

```
Preferred nucleic acids according to the further aspect of the invention may include
SEQ ID No. 23 (cttcgtaaacttcgtaaacgtcttctt), SEQ ID No. 24 (cgtcttactcgtaaacgtggtcttaaa), SEQ ID No. 25 (cttcgtaaacgtcttcttcttcgtaaacttcgtaaacgtcttctt), SEQ ID No. 26 (caatctactgaagaacttcgtgttcgtcttgctagtcatcttcgtaaacttcgtaaacgtcttctt), SEQ ID No. 27 (cttcgtgttcgtcttgctagtcatcttcgtaaacttcgtaaacgtcttcttcgtgatgctgatgatcttcaaaaacgtct
               tgctgtttatcttcgtgttcgtcttgctagtcatcttcgtaaacttcgtaaacgtcttcttcgtgatgctgatgatcttcaaaaacgtc
               ttgctgtttat), SEQ ID No. 28 (cttcgtaaacttcgtaaacgtcttcttcttcgtaaacttcgtaaacgtcttctt), SEQ ID No. 29 (tggcgtaaatggcgtaaacgttggtggtggcgtaaatggcgtaaacgttggtgg), SEQ ID No. 30 (tggcgtaaatggcgtaaacgttggtggcgtaaatggcgtaaacgttgg), SEQ ID No. 31 (tggcgtaaatggcgtaaacgttggtggcttcgtaaacttcgtaaacgtcttctt), SEQ ID No. 32 (tatcgtaaatatcgtaaacgttattattatcgtaaatatcgtaaacgttattat), SEQ ID No. 33 (cttcgtaaacttcgtaaacgtcttcgtaaacttcgtaaacgt), SEQ ID No. 34 (cgtcttactcgtaaacgtggtcttaaacgtcttactcgtaaacgtggtcttaaa), SEQ ID No. 35 (cgtactcgtaaacgtggtcgtcgtactcgtaaacgtggtcgt), SEQ ID No. 36 (cttcgtaaacgtaaacgtcttcttcgtaaacgtaaacgtctt),
```

-continued

SEQ ID No. 37 (cttcgtaaacgtaaacgtcttcgtaaacttcgtaaacgtaaacgtcttcgtaaa), and

SEQ ID No. 38 (tggcgttggcgtaaacgttggcgtaaatggcgttggcgtaaacgttggcgtaaa).

Preferred nucleic acids further include those corresponding DNA molecules encoding any preferred polypeptides according to the invention.

It will be appreciated that, due to redundancy in the genetic code, a nucleic acid sequence in accordance with the invention may vary from the naturally occurring sequence (e.g. in the ApoB or ApoE genes) providing a codon encodes a polypeptide, derivative or analogue thereof in accordance with the first, second or third aspect of the invention.

Other modifications in polypeptide sequences are also envisaged and within the scope of the claimed invention, i.e. those which occur during or after translation, e.g. by acetylation, amidation, carboxylation, phosphorylation, proteolytic cleavage or linkage to a ligand.

It will be appreciated that polypeptides, derivatives and analogues according to the invention represent favourable agents to be administered by techniques involving cellular expression of nucleic acid sequences encoding such molecules. Such methods of cellular expression are particularly suitable for medical use in which the therapeutic effects of the polypeptides, derivatives and analogues are required over a prolonged period.

Thus according to a further aspect of the present invention there is provided a nucleic acid sequence according to the previous aspect of the invention for use as a medicament.

According to a further aspect, there is provided use of the nucleic acid, for the preparation of medicament for treating a bacterial infection.

The nucleic acid may preferably be an isolated or purified nucleic acid sequence. The nucleic acid sequence may preferably be a DNA sequence.

The nucleic acid sequence may further comprise elements capable of controlling and/or enhancing its expression. The nucleic acid molecule may be contained within a suitable vector to form a recombinant vector. The vector may for example be a plasmid, cosmid or phage. Such recombinant vectors are highly useful as delivery systems for transforming cells with the nucleic acid molecule.

Recombinant vectors may also include other functional elements. For instance, recombinant vectors can be designed such that the vector will autonomously replicate in the cell. In this case elements that induce nucleic acid replication may be required in the recombinant vector. Alternatively, the recombinant vector may be designed such that the vector and recombinant nucleic acid molecule integrates into the genome of a cell. In this case nucleic acid sequences, which favour targeted integration (e.g. by homologous recombination) are desirable. Recombinant vectors may also comprise DNA coding for genes that may be used as selectable markers in the cloning process.

The recombinant vector may also further comprise a promoter or regulator to control expression of the gene as required.

The nucleic acid molecule may (but not necessarily) be one, which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the required therapeutic effect has been achieved).

The delivery system may provide the nucleic acid molecule to the subject without it being incorporated in a vector. For instance, the nucleic acid molecule may be incorporated within a liposome or virus particle. Alternatively a "naked" nucleic acid molecule may be inserted into a subject's cells by a suitable means, e.g. direct endocytotic uptake.

The nucleic acid molecule may be transferred to the cells of a subject to be treated by transfection, infection, microinjection, cell fusion, protoplast fusion or ballistic bombardment. For example, transfer may be by ballistic transfection with coated gold particles, liposomes containing the nucleic acid molecule, viral vectors (e.g. adenovirus) and means of providing direct nucleic acid uptake (e.g. endocytosis) by application of the nucleic acid molecule directly.

It will be appreciated that the polypeptides, agents, nucleic acids or derivatives according to the present invention may be used in a monotherapy (i.e. use of polypeptides, agents, nucleic acids or derivatives according to the invention alone to prevent and/or treat a bacterial infection). Alternatively, polypeptides, agents, nucleic acids or derivatives according to the invention may be used as an adjunct, or in combination with known therapies.

In accordance with a further aspect of the invention, there is provided a method of preventing and/or treating a bacterial infection, comprising administering to a subject in need of such treatment a therapeutically effective amount of a polypeptide, derivative, or analogue or nucleic acid according to the invention.

Polypeptides, agents, nucleic acids or derivatives according to the invention may be combined in compositions or compounds having a number of different forms depending, in particular, on the manner in which the composition is to be used. Thus, for example, the composition may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle of the composition of the invention should be one which is well tolerated by the subject to whom it is given, and preferably enables delivery of the polypeptides, agents, nucleic acids or derivatives to the brain. It is preferred that the polypeptides, agents, nucleic acids or derivatives according to the invention be formulated in a manner that permits their passage across the blood brain barrier.

Compositions comprising polypeptides, agents, nucleic acids or derivatives according to the invention may be used in a number of ways. For instance, oral administration may be required in which case the compound may be contained within a composition that may, for example, be ingested orally in the form of a tablet, capsule or liquid. Alternatively, the composition may be administered systemically by injection into the blood stream. Injections may be intravenous (bolus or infusion) or subcutaneous (bolus or infusion). The compounds may be administered by inhalation (e.g. intranasally).

Compositions comprising polypeptides, agents, nucleic acids or derivatives according to the invention may be orally administered or systemically administered. Furthermore, compositions may be administered by aerosol, for example, using an atomiser, which may be administered nasally, or by an inhaler via the lungs. Alternatively, the compositions may be topically applied, for example, in the form of a cream or gel. Topical administration is useful when a subject to be treated has a bacterial skin infection. The composition may be applied intravaginally (for example, if required to protect the subject from sexually transmitted diseases), or rectally.

Polypeptides, agents, nucleic acids or derivatives may also be incorporated within a slow or delayed release device. Such devices may, for example, be inserted on or under the skin, and the compound may be released over weeks or even months. Such devices may be particularly advantageous when long term treatment with a polypeptide, agent, nucleic acid or derivative according to the invention is required and which would normally require frequent administration (e.g. at least daily injection).

It will be appreciated that the amount of a polypeptide, agent, nucleic acid or derivative that is required is determined by its biological activity and bioavailability which in turn depends on the mode of administration, the physicochemical properties of the polypeptide, agent, nucleic acid or derivative employed and whether the polypeptide, agent, nucleic acid or derivative is being used as a monotherapy or in a combined therapy. The frequency of administration will also be influenced by the above-mentioned factors and particularly the half-life of the polypeptide, agent, nucleic acid or derivative within the subject being treated.

Optimal dosages to be administered may be determined by those skilled in the art, and will vary with the particular polypeptide, agent, nucleic acid or derivative in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of polypeptides, agents, nucleic acids or derivatives according to the invention and precise therapeutic regimes (such as daily doses of the polypeptides, agents, nucleic acids or derivatives and the frequency of administration).

Generally, a daily dose of between 0.01 µg/kg of body weight and 0.5 g/kg of body weight of polypeptides, agents, nucleic acids or derivatives according to the invention may be used for the prevention and/or treatment of a viral infection, depending upon which specific polypeptide, agent, nucleic acid or derivative is used. More preferably, the daily dose is between 0.01 mg/kg of body weight and 200 mg/kg of body weight, and most preferably, between approximately 1 mg/kg and 100 mg/kg.

Daily doses may be given as a single administration (e.g. a single daily injection). Alternatively, the polypeptide, agent, nucleic acid or derivative used may require administration twice or more times during a day. As an example, polypeptides, agents, nucleic acids or derivatives according to the invention may be administered as two (or more depending upon the severity of the condition) daily doses of between 25 mg and 7000 mg (i.e. assuming a body weight of 70 kg). A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

This invention provides a pharmaceutical composition comprising a therapeutically effective amount of a polypeptide, agent, nucleic acid or derivative according to the invention and optionally a pharmaceutically acceptable vehicle. In one embodiment, the amount of the polypeptide, agent, nucleic acid or derivative is an amount from about 0.01 mg to about 800 mg. In another embodiment, the amount of the polypeptide, agent, nucleic acid or derivative is an amount from about 0.01 mg to about 500 mg. In another embodiment, the amount of the polypeptide, agent, nucleic acid or derivative is an amount from about 0.01 mg to about 250 mg. In another embodiment, the amount of the polypeptide, agent, nucleic acid or derivative is an amount from about 0.1 mg to about 60 mg. In another embodiment, the amount of the polypeptide, agent, nucleic acid or derivative is an amount from about 0.1 mg to about 20 mg.

This invention provides a process for making a pharmaceutical composition comprising combining a therapeutically effective amount of a polypeptide, agent, nucleic acid or derivative according to the invention and a pharmaceutically acceptable vehicle. A "therapeutically effective amount" is any amount of a polypeptide, agent, nucleic acid or derivative according to the invention which, when administered to a subject provides prevention and/or treatment of a viral infection. A "subject" is a vertebrate, mammal, domestic animal or human being.

A "pharmaceutically acceptable vehicle" as referred to herein is any physiological vehicle known to those of ordinary skill in the art useful in formulating pharmaceutical compositions.

In a preferred embodiment, the pharmaceutical vehicle is a liquid and the pharmaceutical composition is in the form of a solution. In another embodiment, the pharmaceutically acceptable vehicle is a solid and the composition is in the form of a powder or tablet. In a further embodiment, the pharmaceutical vehicle is a gel and the composition is in the form of a cream or the like.

A solid vehicle can include one or more substances, which may also act as flavouring agents, lubricants, solubilisers, suspending agents, fillers, glidants, compression aids, binders or tablet-disintegrating agents; it can also be an encapsulating material. In powders, the vehicle is a finely divided solid that is in admixture with the finely divided active polypeptide, agent, nucleic acid or derivative. In tablets, the active polypeptide, agent, nucleic acid or derivative is mixed with a vehicle having the necessary compression properties in suitable proportions and compacted in the shape and size desired. The powders and tablets preferably contain up to 99% of the active polypeptide, agent, nucleic acid or derivative. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles are used in preparing solutions, suspensions, emulsions, syrups, elixirs and pressurized compositions. The active polypeptide, agent, nucleic acid or derivative can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmoregulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal, intravenous and particularly subcutaneous, intracerebral or intracerebroventricular injection. The polypeptide, agent, nucleic acid or derivative may be prepared as a sterile solid composition that may be dissolved or suspended at the time of administration using sterile water, saline, or other appropriate sterile injectable medium. Vehicles are intended to include necessary and inert binders, suspending agents, lubricants, flavourants, sweeteners, preservatives, dyes, and coatings.

Polypeptides, agents, nucleic acids or derivatives according to the invention can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

Polypeptides, agents, nucleic acids or derivatives according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The polypeptides, agents, nucleic acids or derivatives may be used to treat any mammal, for example, human, livestock, pets, and may be used in other veterinary applications.

The inventors have realised that the polypeptides according to the invention may be used as a medicament but may also be put to a number of other antimicrobial uses (whether in a clinical context or otherwise). For instance, in addition to administering the said polypeptides, agents, nucleic acids or derivatives according to the invention to a patient, they may be used to coat surfaces and objects to prevent or treat bacterial contamination.

Therefore, in a further aspect there is provided a method of preventing and/or treating a bacterial contamination comprising coating an object or a surface in need thereof with an amount of a polypeptide according to the first, second or third aspect of the invention, that is effective for killing or preventing growth of bacteria.

It will be appreciated that the polypeptide may be particularly useful for coating surfaces or objects that are required to be aspectic. As discussed above, many of the polypeptides have the advantage that they are both antiviral and antibacterial. Accordingly the polypeptide will have a broad antimicrobial effect. Furthermore, as discussed in more detail below, the polypeptides are able to adhere to surfaces and are thereby effective for longer periods of time.

The polypeptides may be used to coat any object or device which is used in a biological or medical situation, such as a medical device, and for which it may be important to prevent a bacterial contamination that may lead to any infection in a patient. Examples of medical devices that may be coated according to the invention include lenses, contact lenses, catheters, stents, wound healing dressings, contraceptives, surgical implants and replacement joints.

The polypeptides are particularly useful for coating biomaterials and objects and devices made therefrom. Bacterial contamination/infection of biomaterials can be particularly problematic because the bacterium may use such material as a substrate for growth. Biomaterials (e.g. collagens and other biological polymers) may be used to surface artificial joints. Alternatively certain implants may substantially comprise such biomaterials.

The polypeptides may be used to coat surfaces in environments that are required to be aseptic. For instance the polypeptides may be used in medical environments. The polypeptides may be used to keep hospital wards clean. They may be used to clean surfaces of equipment (e.g. operating tables) in operating theatres as well as theatre walls and floors. The inventors believe the polypeptides will be useful to improve sterility in general and also to address the spread of MRSA in particular (the inventors believe that MRSA may be killed by the polypeptides of the invention).

The polypeptides may be formulated into solutions for cleaning objects and surfaces. For instance, they may be a routine constituent of physiological solutions (for example as a constituent of physiological saline).

Example 3 illustrates how well polypeptides in accordance with the invention adhere to contact lenses. Furthermore, Example 2 illustrates that the peptides are able to surprisingly retain their antibacterial activity even following autoclaving. This is most advantageous when the peptides are used to coat objects that, in use, experience high temperatures and pressures. Furthermore, it will be appreciated that many medical devices such as surgical instruments, need to be sterilised between uses, normally by autoclaving. Hence, the peptides according to the invention are very useful as they (i) adhere to a surface; and (ii) retain their antibacterial activity following sterilisation.

It will be appreciated that the above list of objects and surfaces to which the polypeptides according to the invention may be applied is not exhaustive. Hence, the polypeptides may be administered to any surface, which is prone to a bacterial contamination, for example, kitchen and bathroom surfaces and products, such as a toilet seat, or the toilet itself.

In a preferred embodiment, the polypeptides may be included in saline solution used to store contact lenses.

Preferred polypeptides according to the invention are highly positively charged. This makes them particularly suited for coating surfaces and objects to prevent growth of broad categories of bacteria. Example 3 and FIGS. 8 and 9, clearly illustrate how well the polypeptides in accordance with the invention adhere to a range of different surfaces, ie. glass (cover slips), glass previously coated with the biomaterial Poly(lactide-co-glycolide) (PLGA), and contact lenses.

Preferably, coating of the object or surface may be carried out by preparing an aqueous solution at an appropriate pH and temperature for the said polypeptides according to the invention. The object or surface is exposed to the said solution for sufficient time to allow immobilisation or absorption of a suitable quantity of the polypeptides to the surface thereof or to allow sufficient time to kill the bacterium.

In a preferred embodiment, a sufficiently concentrated solution of a polypeptide according to the invention is prepared, and contacted with the object to be coated for a suitable period of time. The skilled technician will appreciate how to make a polypeptide solution of the required concentration, as this will depend on the particular polypeptide being used and the bacteria to be treated, and the surface being coated. For example, the object may be inserted in the solution (e.g. comprising about 40 μM of the polypeptide) and left for about 15 minutes at about 20° C. Following exposure to the polypeptide, the object may be washed, for example, in a suitable buffer, such as, PBS. It may be required to leave the object in the wash buffer overnight. Following washing, the polypeptide has then adhered to the object, and the object, coated with the protective polypeptide, is ready for use.

In addition, the inventors have found that contact lenses, when pre-incubated with the polypeptides according to the invention, become resistant to bacterial infection as is illustrated in FIGS. 2, 3 and 4.

According to a further aspect of the invention there is provided a contact lens at least partially coated with a polypeptide according to the first, second or third aspects of the invention.

The polypeptide applied to the surface of the contact lens prevents bacterial contamination occurring that can results in infections occurring in the eye of the user.

In one embodiment, the lens may be a one day disposable lens (i.e. worn for one day and then disposed of), in which case, bacterial contamination is obviated before the lens is used and also when removed from its package. Accordingly, the lens my be pretreated with the polypeptide and/or may be packaged in a solution containing the polypeptide. The lens coated with the polypeptide reduces the likelihood of a bacterial infection in the user than may occur while the contact lens is being worn.

Alternatively, a lens may be repeatedly worn on a daily basis for several months or years, but taken out and washed and stored in solution over night. When this is the case a polypeptide coating on the lens (before first use) and/or preferably use of the polypeptides in lens wash solutions, will significantly reduce the likelihood of a bacterial infection of the user occurring while the lens is being worn, or the lens being contaminated while it is being stored and washed overnight.

In another embodiment, the lens may be an extended wear lens, which is constantly worn in the eye for extended periods of time, for example, more than one day, several days, a week or even a month or more. Users of such contact lenses have a high risk of developing a bacterial infection. Hence, in this case, the polypeptide may be used to coat the lens before it is first used. Use of such a coated lens will greatly reduce the likelihood of a bacterial infection occurring while the lens is being worn for such extended periods of time.

In a preferred embodiment, a contact lens is coated with a polypeptide according to the invention, and where appropriate, stored and/or washed in a solution comprising the polypeptide.

The inventors have further established that several polypeptides, agents, nucleic acids or derivatives according to the invention may be combined and used to prevent or treat a broad range of bacterial infections/contaminations (as well as viral infections/contaminations). For example, it may be preferred to treat a bacterial infection/contamination with a combination of polypeptides according to any one of the first, second, or third aspects, such as a polypeptide independently selected from a group consisting of GIN 1p, GIN 7, GIN 32, GIN 33 and GIN 34. However, it will be appreciated that different combinations of polypeptides can be used to treat different bacterial infections.

Furthermore, the polypeptides, agents, nucleic acids or derivatives according to the invention may be used to minimise, prevent or treat bacterial contamination or bacterial growth, by use as, or in conjunction with, a preservative. Hence, the polypeptides, agents, nucleic acids or derivatives may be used as a preservative in foodstuffs. In addition, the polypeptides, agents, nucleic acids or derivatives may be used to minimise or prevent bacterial growth in cultures, for example, in tissue culture work, either to supplement, or to replace antibiotics. In addition, the polypeptides may be used as selective agents as a diagnostic agent, for example, for bacterial growth in culture media. For example, a first polypeptide may be added to media, which is particularly active against a first bacterium, and a second polypeptide may be added to the media, which is particularly active against a second bacterium.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Embodiments of the invention will now be further described, by way of example only, with reference to the following Example and figures in which:—

FIG. 5 illustrates MTT reduction in cells treated with various levels of GIN peptides for 48 hours;

FIGS. 6A, 6B & 6C illustrate the lack of genotoxic effects of peptides GIN 1p, GIN 33 and GIN 34, respectively, as indicated by a yeast genotoxicity assay;

FIG. 7 illustrates the level of growth of *Pseudomonas aeruginosa* after exposure of a bacterial inoculum to various concentrations of peptide GIN 1p in accordance with the present invention, which had been either autoclaved or without autoclaving, expressed as a % of growth for untreated bacteria;

Figure 9:
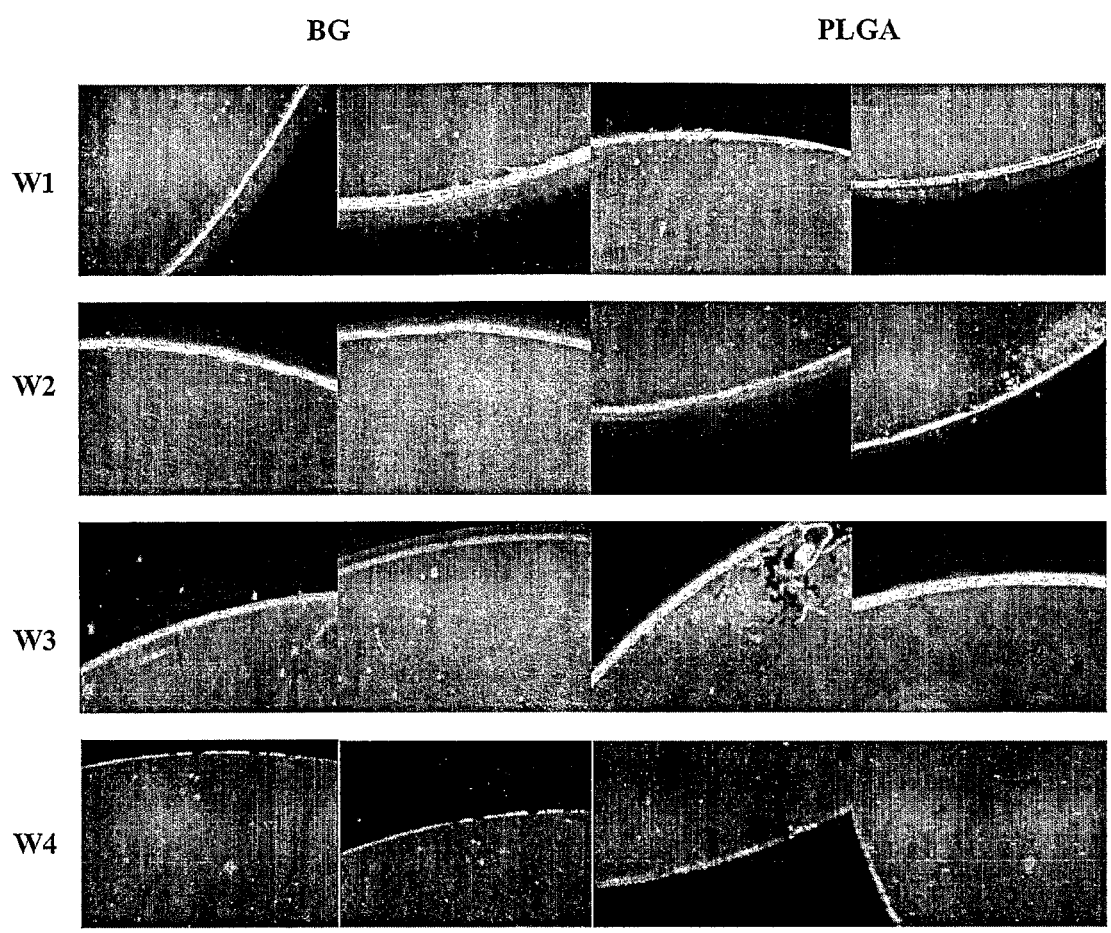

FIG. 8 illustrates Johnson and Johnson Acuvue contact lenses, which had been treated for 15 min with 40 μM GIN1p (which had been synthesised with the addition of a cysteine residue having a fluorescent tag), then washed 4 times, including an overnight soak in 25 ml PBS;

FIG. 9 illustrates glass cover slips (BG), or cover slips previously coated with the biomaterial Poly(lactide-co-glycolide) (PLGA), which had been treated for 15 min with 40 μM GIN1p (which had been synthesised with a fluorescent tag), then washed 4 times, including an overnight soak in 25 ml PBS;

FIG. 10 shows typical mass spectrometry data for GIN1p, and illustrates that the peptide was >95% purity; and FIG. 11 shows typical HPLC data for GIN1p, and illustrates that the peptide was >95% purity.

EXAMPLES

The inventors carried out a number of experiments to investigate the antibacterial activity of polypeptides according to the invention. The activity of the polypeptides against *Staphylococcus aureus, Pseudomonas aeruginosa*, and *Streptococcus pneumoniae* was investigated, as well as the antibacterial activity of the polypeptides on contact lenses. Furthermore, the inventors carried out toxicity and genotoxicity tests, and also investigated whether the polypeptides retained their antibacterial activity following exposure to high temperatures, i.e. following autoclaving. In addition, the inventors investigated the ability of the polypeptides to adhere to a variety of surfaces, for example, contact lenses, glass and surfaces coated with the biomaterial "PLGA".

Example 1

Antibacterial Efficacy Assessment

Bacterial Stocks—ATCC derived stock bacteria were obtained from Oxoid Limited. *Pseudomonas aeruginosa* (ATCC strain 9027) or *Staphylococcus aureus* (ATCC strain 6538P) were obtained in 'Cultiloop' format. Stocks were prepared by inoculating 20 ml of LB broth with a single Cultiloop, and incubating overnight at 37° C. Cells present after overnight incubation were harvested by removing larger aggregates by centrifugation (3000 g, 10 minutes), and withdrawing 16 ml of the supernatant, which was likely to contain mainly planktonic bacteria. To this, 4 ml of sterile glycerol was added (the latter having been sterilised by autoclaving). The resultant suspension was divided between 15× 1 ml cryovials before freezing at −85° C.

Antibacterial Assay

Preliminary experiments were carried out to estimate the amount to dilute bacterial stocks which when on addition of 25 µl of diluted stock to 100 µl of fresh LB broth would result in bacteria in log phase growth after overnight incubation at 37° C. This was found to correspond to around 40,000 cfu per well at inoculation.

Peptides

Peptides (including polypeptides according to the invention) were obtained in lyophilised form from a commercial supplier (AltaBioscience, University of Birmingham), and were produced at 5 micromole scale. The skilled technician will know the standard techniques, which are available for synthesising peptides, once they have been given the amino acid sequence of the peptide. N-terminals were protected by addition of an acetyl group, and the C-terminals were protected by addition of an amide group. Small quantities of peptide were weighed in sterile Eppendorf tubes, before addition of sufficient PBSA to produce a 0.4 mM stock solution, which was frozen at −85° C. in aliquots.

Molecular weight of peptides was confirmed by laser desorption mass spectrometry using a Finnigan LASERMAT 2000 MALDI-time of flight mass analyzer or a Scientific Analysis Group MALDI-TOF mass spectrometer. HPLC purification of peptides was performed using a Vydac analytical C-4 reverse phase column, using 0.1% TFA and 0.1% TFA/80% acetonitrile as solvents, or for some peptides an ACE C18 Reverse Phase column, using 0.05% TFA and 60% acetonitrile as solvents. Typical mass spectrometry data and high performance liquid chromatography (HPLC) traces (purity >95%) for peptide GIN1p are shown in FIGS. 10 and 11.

(a) Antibacterial Efficacy Against *Staphylococcus aureus*

The peptides were examined for antibacterial efficacy against *Staphylococcus aureus*. The results are shown in Table 5. To test the efficacy of peptides, dilutions of test peptides or PBS (for use as a control) were prepared in LB broth, and 100 µl aliquots of these placed in 96-well plates. A vial of planktonic bacterial stock was thawed in a 37° C. incubator and diluted to the level previously determined which would produce log phase growth after overnight incubation (see above). 25 µl of this bacterial dilution was then added to the test wells (some wells containing LB broth without peptide were left without any bacterial inoculation, these being used as a blank). After overnight growth, the concentration of bacteria in individual wells was assessed by measuring absorbance at 620 nm, in a microplate spectrophotometer. The average absorbance of wells for specific concentrations of peptides was calculated, and from this the percentage inhibition (relative to untreated wells) was also calculated and plotted against concentration (along with an estimate of error on that % inhibition). Finally, the approximate concentration of peptide inhibiting bacterial growth by 50% was estimated from this figure to calculate the $IC_{50}$ value.

The efficacy of tested peptides are shown in Table 5. Any peptide with an $IC_{50}$ value of less than or equal to about 40 µM was considered to be ineffective.

TABLE 5

Activity of apoE-derived peptides against *Staphylococcus aureus*

| Peptide Reference | IC50 (µM) | Sequence |
|---|---|---|
| GIN 34 | 7 | WRKWRKRWWLRKLRKRLL |
| GIN 33 | 9.5 | WRWRKRWRKWRWRKRWRK |
| GIN 32 | 10 | WRKWRKRWRKWRKR |
| GIN 1p | 13 | LRKLRKRLLLRKLRKRLL |
| GIN 7 | 19 | WRKWRKRWWWRKWRKRWW |
| GIN 41 | 33 | YRKYRKRYYYRKYRKRYY |

Sequences where no activity could be detected:-

| Peptide Reference | Sequence |
|---|---|
| GIN 6 | ERKERKREEERKERKREE |
| GIN 22 | DWLKAFYDKVAEKLKEAF |
| GIN 39 | ARKARKRAAARKARKRAA |

Table 5 illustrates that polypeptides according to the first, second or third aspect of the invention had good antibacterial efficacy whereas peptides that fall outside the scope of the invention (e.g. GIN 6, 22 or 39) were not effective.

(b) Antibacterial Efficacy Against *Pseudomonas aeruginosa*

Peptides in accordance with the invention were also examined for antibacterial efficacy against *Pseudomonas aeruginosa* using the same technique as described above to calculate the $IC_{50}$ values. The peptides according to the invention, which were tested are shown in Table 6.

TABLE 6

Activity of apoE-derived peptides against *Pseudomonas aeruginosa*

| Peptide Reference | IC50 (µM) | Sequence |
|---|---|---|
| GIN 1p | 3 | LRKLRKRLLLRKLRKRLL |
| GIN 34 | 3 | WRKWRKRWWLRKLRKRLL |
| GIN 7 | 5 | WRKWRKRWWWRKWRKRWW |

TABLE 6-continued

| GIN 32 | 5   | WRKWRKRWRKWRKR |
| GIN 2  | 8.5 | LRKRLLLRKLRKRLL |
| GIN 8  | 9.2 | LRKLRKRLRKLRKR |
| GIN 33 | 12  | WRWRKRWRKWRWRKRWRK |
| GIN 11 | 15  | QSTEELRVRLASHLRKLRKRLL |

Sequences where no activity could be detected:

| Peptide Reference | Sequence |
|---|---|
| GIN 6  | ERKERKREEERKERKREE |
| GIN 10 | RLLRLLRLLRLLRLLRLL |
| GIN 12 | LRKLRKRLLRDADDLQKRLA |
| GIN 22 | DWLKAFYDKVAEKLKEAF |
| GIN 28 | LRKEKKRLLLRKEKKRLL |
| GIN 39 | ARKARKRAAARKARKRAA |
| GIN 43 | LRYLRYRLLLRYLRYRLL |

Table 6 further illustrates that polypeptides according to the first, second or third aspect of the invention had good antibacterial efficacy whereas peptides that fall outside the scope of the invention (e.g. GIN 6, 10, 12, 22, 28, 39 or 43) were not effective.

Figure 1:
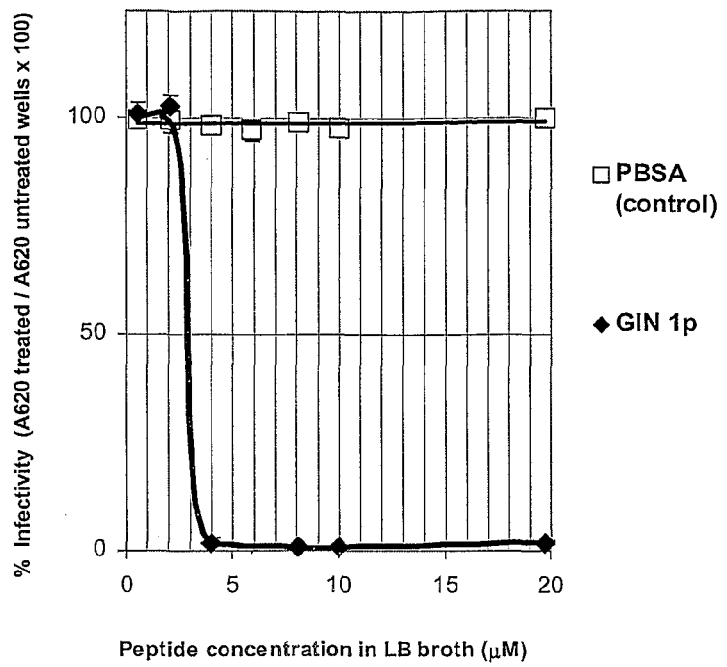
FIG. 1 illustrates the level of growth of *Pseudomonas aeruginosa* after exposure of a bacterial inoculum to various concentrations of peptide GIN 1p in accordance with the present invention, or of a dummy dilution of PBSA.

Referring to FIG. 1, there is shown the level of growth of *Pseudomonas aeruginosa* after exposure of a bacterial inoculum to various concentrations of GIN 1p (a polypeptide in accordance with the present invention), or of a dummy dilution of PBSA. Points were obtained by dividing the average for six treated wells by the average for six untreated wells, and bars show an estimate of the error for these calculated values. FIG. 1 clearly shows the antibacterial efficacy of GIN 1p (SEQ ID No. 6) at a concentration of approx. 4 µM and indicates that GIN 1p has an $IC_{50}$ concentration of approximately 3 µM.

In summary, the polypeptides according to the invention exhibit antibacterial activity against both *S. aureus*, and *P. aeruginosa*.

(c) Coating with Antibacterial Polypeptides

Polypeptides according to the invention may be used to coat medical devices prone to contamination with bacteria. Examples of such medical devices include lenses, catheters, stents, wound healing dressings and contraceptive devices. The polypetides may also be applied to surfaces in medical environments, including surfaces of equipment for use in operating theatres.

Coating a surface can be carried out by preparing a concentrated aqueous solution of polypeptide (for example 200 µM) at an appropriate pH (for example pH7.4) for the specific polypeptide. A surface is then exposed to the aqueous solution at a suitable temperature (for example 37° C.) for sufficient time (for example 2 hours) to allow immobilisation or absorption of a suitable quantity of the polypeptide to the surface thereof.

(d) Experiment to Test Antibacterial Efficacy on Contact Lenses

Figure 2:
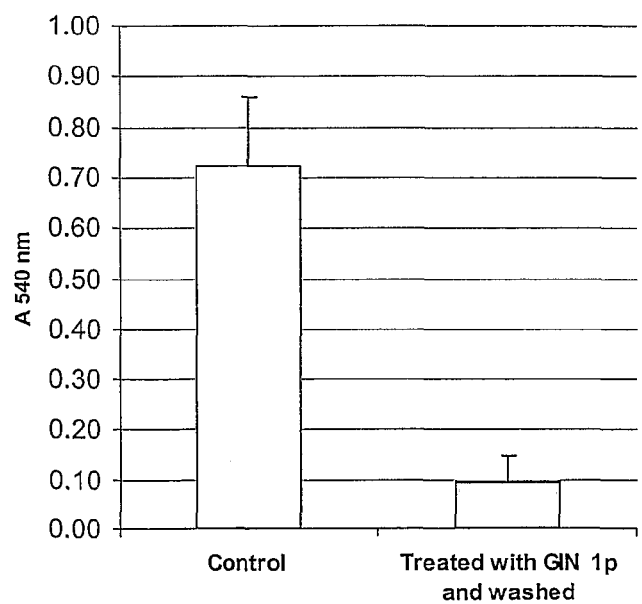
FIG. 2 is a bar graph illustrating growth of *Pseudomonas aeruginosa* overnight on Johnson and Johnson Acuvue contact lenses following pre-treatment with peptide GIN 1p, or a control treatment.

The inventors have found that contact lenses, when pre-incubated with solutions of the polypeptides in accordance with the invention, become resistant to bacterial infection. Referring to FIG. 2, there is shown a bar graph illustrating growth of *Pseudomonas aeruginosa* overnight on Johnson and Johnson Acuvue contact lenses following pre-treatment with polypeptide GIN 1p, or a control treatment. Growth was measured by examination by light microscopy, and by assessing metabolic activity of any bacteria present using MTT reduction. The data illustrates the efficacy of the antibacterial nature of the peptides according to the invention when applied to contact lenses. Antibacterial activity was assessed by measuring MTT reduction.

Lenses were placed in 24-well plates before treatment with 75 µl of 250 µM GIN-1p in PBS (pH7.4) or with 75 µl of PBS and incubated for 2 hours at 370° C., before removal of these solutions from the lens by aspiration. A further 1 ml of PBS was then added to the wells to wash away any loosely attached peptide, before aspiration of this wash solution. Finally, 1 ml of 20% (v/v) LB broth in PBS was added to each well, the latter containing $10^4$ challenge organisms (an amount which approximates to the likely level of challenge which would be appropriate for the eye). Calculations suggest that even if aspiration of the initial polypeptide solution or wash solution was not complete, the concentration of polypeptide carried over and still present in the system in solution (i.e. merely as a dilution of the original peptide stock) would be less than 200 nM, which would be too low on its own to inhibit bacterial infection.

The plates were returned to the incubator at 37° C. overnight. After approximately 15 hr incubation, some of the lenses were exposed to MTT solution at 2 mg/ml, and incubated for a further one hour at 37° C. The remaining lenses were examined both using a light microscope (Olympus IX70) or examined without magnification. The MTT treated lenses were removed from the MTT solution after the further incubation, and placed in 1 ml DMSO, to solubilise any blue formazan crystals produced by due to the metabolic activity of any bacteria present. The degree of formazan production was assessed by measuring absorbance at 540 nm for aliquots of these solutions; these values are shown in FIG. 2, and represent the average for four lenses, with the bars showing standard deviation.

Figure 3:
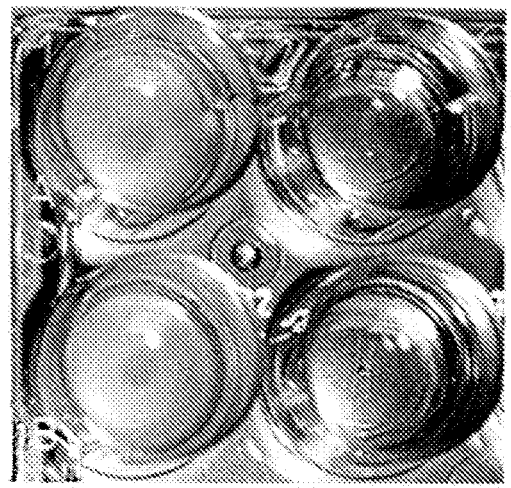
FIG. 3 is a photograph showing the appearance of two GIN1p-treated and two control-treated contact lenses positioned in four wells of a 24-well plate after overnight incubation.

Referring to FIG. 3, there is shown a photograph showing the appearance of two GIN1p-treated contact lenses (right hand side of FIG. 3) and two control-treated contact lenses (left hand side of FIG. 3) positioned in four wells of a 24-well plate after overnight incubation. The Figure clearly shows that the two GIN1p-treated contact lenses are less prone to developing a bacterial infection. The reaction solution containing the two control lenses, which were not pre-treated with a polypeptide according to the invention, are cloudy, indicating that bacteria are growing therein. However, the solutions containing the two GIN1p pre-treated contact lenses are colourless, indicating that the majority of any bacterial growth has been minimised.

Figure 4:
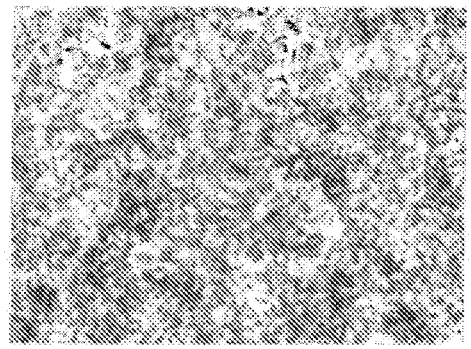
FIG. 4 is a light micrograph showing the appearance of the surface of a (i) control-treated or a (ii) GIN1p-treated contact lens after overnight incubation.

Referring to FIG. 4, there is shown a light micrograph showing the appearance of the surface of the (i) control-treated contact lens, and the (ii) GIN1p-treated contact lens after overnight incubation. FIG. 4 clearly shows that the control-treated lens is covered with bacterial growth, whereas the GIN1p-treated lens show minimal bacterial growth. Hence, the polypeptide GIN1p, in accordance with the invention, clearly exhibits antibacterial activity.

Hence, the inventors suggest that any method of immobilisation of these polypeptides on lenses in an active anti-microbial form will reduce the risk of microbe related adverse reactions in contact lens wearers, such as microbial keratitis.

(e) Toxicity Assays

Referring to FIG. 5, there is shown MTT reduction in cells treated with various levels of GIN 1p and GIN 16 for 48 hours.

African Green Monkey Kidney (Vero) cells were maintained in Eagle's minimum essential medium with Earle's salt (EMEM) and supplemented with 10% fetal calf serum (heat-inactivated), 4 mM L-glutamine, and 1% (v/v) non-essential amino acids, plus penicillin and streptomycin (100 IU/mg and 100 mg/ml, respectively) (maintenance medium referred to as 10% EMEM). The cells were incubated at 37° C. in a humidified atmosphere of air with 5% $CO_2$. On harvesting, monolayers were washed in phosphate-buffered saline (PBS), and dislodged by incubating with trypsin in PBS for 30 min, before inactivating trypsin by addition of an equal volume of 10% EMEM and centrifuging at 500 g (5 min, 4° C.).

Vero cells were seeded in 96-well plates at 30,000 cells per well in 100 µl of 10% EMEM. After overnight growth, medium was gently aspirated and replaced with 10% EMEM containing various concentrations of peptides or in some cases just 10% EMEM alone. Cells were returned to the incubator for 48 hr, before addition of 25 µl of 1.5 mg/ml MTT solution (prepared in 0.5% EMEM, then filtered though a sterile 0.22 µm filter). The plates were then returned to the incubator for one hour. Finally, medium was removed from wells, and any blue formazan crystals solubilised by addition of 100 µl of dimethylsulphoxide (DMSO). Absorbance of resulting solutions was then measured at 570 nm, and toxic effect expressed as a percentage of the control value for each peptide concentration. Where possible, the EC50 was calculated from plots of toxic effect against peptide concentration. Fortunately, no evidence of toxicity was found for the cell line tested, using peptide at 40 µM exposed to cells for 2 days.

(f) Genotoxicity

Additionally, the inventors have found that despite the high numbers of positive charges on these peptides, they have little or no genotoxic activity, as revealed by the Gentronix Green-Screen GC genotoxicity assay (Gentronix Ltd., 72 Sackville St, Manchester, M60 1QD, UK), which was used to test the peptides GIN1p, GIN 33 and GIN 34, and as summarised in FIGS. 6A-6C.

A liquid handling robot is used to produce a serial dilution series of each test compound in a 96-well, black microplate with an optically clear base. Each dilution of the test compound is combined with an equal volume of a specialised growth medium containing Saccharomyces cerevisiae yeast cells (strain GenT01: see Mutation Research, 2000, 464 297-308 for details of the properties of these modified strains) to give a fixed final volume and concentration of cells. In addition, a series of genotoxic and cytotoxic standards and non-toxic controls are run to provide internal quality control. The plates are covered with a breathable membrane and incubated overnight, without shaking, at 25° C.

After incubation, the microplates are uncovered and data collected using a Tecan Ultra 384 microplate reader. This instrument provides measurements of light absorbance and fluorescence in microplates; a standard fluorescein filter set (excitation 485/25 and emission 535/25) is used. Absorbance is read at 620 nm and is proportional to cell proliferation (which is lowered by toxic analytes). Fluorescence is proportional to the activity of the DNA repair system (increased by genotoxic analytes). The yeast cultures used are a genetically modified strain that express a green fluorescent protein whenever the cells carry out DNA damage repair. Fluorescence is normalised to the absorbance signal to correct for variation in cell yield caused by any cytolytic activity of the test compounds against the yeast cells. This produces a "fluorescence per cell" measurement termed "brightness". In addition to the Gentronix Assay yeast strain (GenT01), a control Saccharomyces cerevisiae strain (GenC01) is also used, which is identical except for its ability to produce green fluorescent protein is disabled. This strain is used to provide a control to allow correction for substances which may be either autofluorescent themselves or which induce an autofluorescence in the yeast cells. The data collected is simply transferred into a Excel template where result evaluation sheets are automatically produced. The sheets contain the processed results in both a graphical and tabulated format, with automatic assessment of the result, i.e. positive or negative, and calculation of the lowest effective concentration (LEC), for both genotoxicity and cytotoxicity.

Referring to FIGS. 6A-6C, there are shown yeast genotoxicity assay obtained for polypeptides GIN 1p, GIN 33 and GIN34, respectively. The control strain (GenC01) behaved as expected with little autofluorescence being apparent in this strain in the presence of the polypeptides, though nonetheless the data obtained using the test strain (GenT01) were corrected to take account of this minimal background. FIGS. 6A-6C show that all three polypeptides failed to produce any genotoxic response in the test yeast strain (GenT01), with values for polypeptide concentrations up to and including 100 µM clearly failing to reach the threshold required for genotoxicity to be indicated.

In conclusion, the results indicate the antibacterial efficacy of the polypeptides in accordance with the present invention. In particular, the polypeptides GIN 34 (SEQ ID No. 12), GIN 33 (SEQ ID No. 16), GIN 32 (SEQ ID No. 8), GIN 1p (SEQ ID No. 6), GIN 7 (SEQ ID No. 7), GIN 41 (SEQ ID No. 10), GIN 2 (SEQ ID No. 3), GIN 8 (SEQ ID No. 11), and GIN 11 (SEQ ID No. 4) exhibited antibacterial activity without any adverse effects on genotoxicity.

Example 2

Polypeptides Retain Efficacy after Autoclaving

To test the effect of treatment of the polypeptides according to the invention by autoclaving, a 400 µM stock solution of GIN1p was prepared in PBS, and 420 µl aliquots were placed in four Eppendorf tubes (with screw lids). After securing the lids, two of the tubes were loaded into a metal rack held within a Pyrex beaker, and placed into a Prestige Medical Clinical Autoclave. The remaining two tubes were left untreated, as a control. The autoclave was then activated, and underwent two autoclave cycles, each of which involved exposure of the peptide solutions to 126° C. for 11 min. Finally, efficacy of the two autoclaved and the two control peptide samples against P. aeruginosa was tested as previously described.

Referring to FIG. 7, there is shown the level of growth of Pseudomonas aeruginosa after exposure of a bacterial inoculum to various concentrations of GIN 1p (a polypeptide in accordance with the present invention) which had been either autoclaved or without autoclaving, expressed as a % of growth for untreated bacteria. As can be seen, the $IC_{50}$ values for all four samples were identical (around 2 µM, as shown in FIG. 7). Accordingly, polypeptides according to the invention are therefore suitable for use with products, which would normally be sterilised by autoclaving during the manufacturing procedure.

Example 3

Polypeptides Adhere to Contact Lenses, Glass and to Surfaces Coated with the Biomaterial "PLGA"

To test whether the peptides according to the invention could be immobilised on a biomaterial or other surfaces, the inventors obtained a fluorescently labelled form of the GIN1p (Advanced Biomedical, Oldham, UK). A 40 µM stock solution of this labelled polypeptide was prepared in PBS, and 250 µl aliquots were inserted in to the wells of a 24-well microplate. The inventors then placed several materials into these peptide solutions, these being: (i) Johnson and Johnson Acuvue contact lenses; (ii) bare glass coverslips; or (iii) coverslips previously coated with the biomaterial Poly(lactide-co-glycolide) (PLGA: coated slides provided by Prof Jian Lu, Department of Physics, University of Manchester).

After incubation at 20° C. for 15 min in the peptide solutions, the materials were removed, and then washed by placing in 1 ml PBS. The materials were then examined by fluorescence microscopy (using an Olympus IX70 inverting microscope fitted with a Chroma 35002v2 filter set), and the results were recorded by photography. The materials were then washed two more times in 1 ml PBS, and then finally left to soak overnight at 37° C. in 25 ml PBS. The level of fluorescence was observed and recorded after each wash, again by microscopic observation and photography as described above.

Referring to FIG. 8, there are shown Johnson and Johnson Acuvue contact lenses, which had been treated for 15 min with 40 µM GIN1p (which had been synthesised with a fluorescent tag), then washed 4 times, including an overnight soak in 25 ml PBS. FIG. 8(a) shows an untreated lens and a GIN1p-treated lens (after 4 washes), under illumination with white light, or GFP fluorescence, using a Olympus IX70 microscope. Hence, even after repeated washing, the lens retains a significant quantity of peptide, such that fluorescence is visible even by eye as shown in FIG. 8(b). The images were captured using a Canon EOS300D digital camera, using ISO1600 film setting, and with a 0.3s exposure time for fluorescent images.

Referring to FIG. 9, there are shown glass cover slips (BG), or cover slips previously coated with the biomaterial Poly(lactide-co-glycolide) (PLGA), which had been treated for 15 min with 40 µM GIN1p (which had been synthesised with a fluorescent tag), then washed 4 times, including an overnight soak in 25 ml PBS. The level of fluorescence was observed using an Olympus IX70 microscope for samples after each wash (W1, W2, W3 and W4). Hence, it can be seen that the level of fluorescence did not decrease noticeably after any of the washes, suggesting that the polypeptide adheres firmly to a range of surfaces. The images were captured using a Canon EOS300D digital camera, with a 5s exposure time using ISO1600 film setting.

Accordingly, FIGS. 8 and 9 show that all three types of material appeared to retain similar levels of GIN1p despite extensive washing, suggesting the polypeptide is suitable for coating various surfaces (as shown in FIG. 8a, and FIG. 9). In particular, the contact lenses were found to absorb significant quantities of the polypeptide (presumably due to their large surface area), such that fluorescence was clearly visible to the naked eye, even after the fourth overnight wash as shown in FIG. 8b.

Example 4

Antibacterial Efficacy Against *P. Aeroginosa*, *S. Aureus*, and *S. Pneumoniae*

The inventor constructed an expanded library of peptides derived from either apolipoprotein B or apolipoprotein E in order to further evaluate polypeptides in accordance with the invention. Further experiments were then conducted to investigate the antibacterial activity of this peptide library against the bacteria *P. aeroginosa*, *S. aureus* and *S. pneumoniae*. The methods used to determine the $IC_{50}$ values for each peptide were as described in the Example 1. In contrast to the $IC_{50}$ values measured in Example 1, values measured in Example 4 were less than or equal to about 60 µm.

Table 7 provides data for peptides that are derived from apoE.

TABLE 7

| Peptides derived from apolipoprotein E | | | | | |
|---|---|---|---|---|---|
| Peptide | SEQ. ID. No. | Sequence | P.aeruginosa IC50 (µM) | S.aureus IC50 (µM) | S.pneumoniae IC50 (µM) |
| MU_1 (GIN 6) | SEQ ID NO. 39 | ERKERKREEERKERKREE | – | – | – |
| MU_2 (GIN 39) | SEQ ID NO. 41 | ARKARKRAAARKARKRAA | – | – | – |
| MU_3 | SEQ ID NO. 59 | DRKDRKRDDDRKDRKRDD | – | – | – |
| MU_4 (GIN 7) | SEQ ID NO. 7 | WRKWRKRWWWRKWRKRWW | 7 | 7 | 24 |
| MU_5 (GIN 40) | SEQ ID NO. 42 | MRKMRKRMMMRKMRKRMM | >53 | >53 | – |
| MU_6 (GIN 41) | SEQ ID NO. 10 | YRKYRKRYYYRKYRKRYY | >53 | >53 | – |
| MU_7 | SEQ ID NO. 48 | FRKFRKRFFFRKFRKRFF | 6 | 11 | – |
| MU_8 | SEQ ID NO. 49 | IRKIRKRIIIRKIRKRII | 45 | >53 | – |
| MU_9 | SEQ ID NO. 50 | QRKQRKRQQQRKQRKRQQ | – | – | – |
| MU_10 (GIN 1p) | SEQ ID NO. 6 | LRKLRKRLLLRKLRKRLL | 3 | 26 | 45 |
| MU_11 | SEQ ID NO. 51 | NRKNRKRNNNRKNRKRNN | – | – | – |

TABLE 7-continued

Peptides derived from apolipoprotein E

| Peptide | SEQ. ID. No. | Sequence | P.aeruginosa IC50 (µM) | S.aureus IC50 (µM) | S.pneumoniae IC50 (µM) |
|---|---|---|---|---|---|
| MU_12 | SEQ ID NO. 52 | CRKCRKRCCCRKCRKRCC | – | – | – |
| MU_13 | SEQ ID NO. 53 | SRKSRKRSSSRKSRKRSS | – | – | – |
| MU_14 | SEQ ID NO. 54 | VRKVRKRVVVRKVRKRVV | – | – | – |
| MU_15 | SEQ ID NO. 55 | TRKTRKRTTTRKTRKRTT | – | – | – |
| MU_16 | SEQ ID NO. 56 | RRKRRKRRRRRKRRKRRR | >53 | – | >53 |
| MU_17 | SEQ ID NO. 57 | GRKGRKRGGGRKGRKRGG | – | – | – |
| MU_18 | SEQ ID NO. 58 | KRKKRKRKKKRKKRKRKK | – | – | – |
| MU_20 | SEQ ID NO. 60 | PRKPRKRPPPRKPRKRPP | – | – | – |
| MU_43 | SEQ ID NO. 61 | MRKLRKRLMMRKLRKRLM | 17 | – | |
| MU_46 | SEQ ID NO. 62 | LRKLRKRLL | 22 | – | >53 |
| MU_58 | SEQ ID NO. 63 | WRKWRKRWWRKWRKRWW | 7.5 | 8 | |
| MU_59 | SEQ ID NO. 64 | WRKWRKRWRKWRKRW | 7.5 | 11 | |
| MU_60 | SEQ ID NO. 65 | WRKWRKRWWFRKWRKRWW | 12.5 | 6 | |
| MU_61 | SEQ ID NO. 66 | WRKWRKRFFWRKWRKRFF | 3 | 5 | |
| MU_81 | SEQ ID NO. 67 | WRKRWWRWRKRWWR | 28 | 20 | |
| MU_82 | SEQ ID NO. 68 | LRKLRKRLLRLRKLRKRLLR | | 13 | |
| MU_83 | SEQ ID NO. 69 | WRKWRKRWWRWRKWRKRWWR | 15 | 9 | |
| MU_111 | SEQ ID NO. 70 | LRKLRKRLLWRKWRKRWW | 12.5 | 7 | |
| MU_112 | SEQ ID NO. 71 | LRKLRKRLLLRKLRKRWW | 7 | 7 | |
| MU_113 | SEQ ID NO. 72 | LRKLRKRLLWRKWRKRLL | | 11 | |
| MU_114 | SEQ ID NO. 73 | WRKWRKRLLLRKLRKRLL | | 5.5 | |
| MU_115 | SEQ ID NO. 74 | WRKLRKRLLLRKLRKRLL | 3 | 9 | |
| MU_116 | SEQ ID NO. 75 | WRKWRKFFFRKWRKRWW | 14 | 6.5 | |
| MU_117 | SEQ ID NO. 76 | WRKWRKRWWFRKFRKRFF | 10 | 7 | |
| GIN 34 | SEQ ID NO. 9 | WRKWRKRWWLRKLRKRLL | 3 | 7 | 20 |
| GIN 32 | SEQ ID NO. 8 | WRKWRKRWRKWRKR | 5 | 13.5 | |
| GIN 08 | SEQ ID NO. 11 | LRKLRKRLRKLRKR | 9.2 | – | >53 |
| GIN 02 | SEQ ID NO. 3 | LRKRLLLRKLRKRLL | 8.5 | – | 26 |
| GIN 05 | SEQ ID NO. 77 | LRKLRKRLLLRK | – | – | – |
| GIN 10 | SEQ ID NO. 78 | RLLRLLRLLRLLRLLRLL | – | | |

From Table 7, it will be seen that the polypeptides in accordance with the present invention show antibacterial activity against at least one, if not two, and if not all three, of the three different bacterial strains evaluated. In particular, MU 4, MU 7, MU 10, MU 43, MU 58, MU 59, MU 60, MU 61, MU 82, MU 83, MU 112, MU 115, and GIN34 are particularly effective. A range of peptides, falling outside the definition of the polypeptides according to the invention, can be seen to be ineffective.

It will be seen that the antibacterial of the polypeptide MU 10 (tandem repeat) is much greater than that of MU43 (monomer), illustrating the surprising property that tandem repeats in accordance with the invention are effective antibacterials. The peptides, which do not show antibacterial activity fall outside the scope of the invention, e.g. MU 3, MU 12, MU 19, GIN 5.

Table 8 presents data for peptides that are derived from apoB.

TABLE 8

Peptides derived from apolipoprotein B

| Peptide | SEQ. ID. No. | Sequence | P.aeruginosa IC50 (μM) | S.aureus IC50 (μM) | S.pneumoniae IC50 (μM) |
|---|---|---|---|---|---|
| MU_24 | SEQ ID NO. 80 | LLRKRLKRLLLRKRLKRL | 7 | 34 | |
| MU_25 | SEQ ID NO. 81 | WRWRRRWRKWRWRRRWRK | >53 | >53 | - |
| MU_26 | SEQ ID NO. 82 | WRWKKKWRKWRWKKKWRK | 52 | 52 | - |
| MU_27 (GIN 33) | SEQ ID No. 16 | WRWRKRWRKWRWRKRWRK | 23 | 15.5 | 46 |
| MU_28 | SEQ ID NO. 83 | RRWRKRWRKWRWRKRWRK | 11.5 | 15 | 46 |
| MU_29 | SEQ ID NO. 84 | KRWRKRWRKWRWRKRWRK | 7.5 | 23 | 52 |
| MU_30 | SEQ ID NO. 85 | LRWRKRWRKWRWRKRWRK | 15 | 15 | 38 |
| MU_31 | SEQ ID NO. 86 | HRWRKRWRKWRWRKRWRK | 12 | 17 | 42 |
| MU_32 | SEQ ID NO. 87 | RWRKRWRKWRWRKRWRK | 12 | 15 | 46 |
| MU_33 | SEQ ID NO. 88 | RRWRKRWRKRRWRKRWRK | >53 | 38 | 53 |
| MU_35 | SEQ ID NO. 89 | LRWRKRWRKLRWRKRWRK | 23 | 31 | 53 |
| MU_36 | SEQ ID NO. 90 | HRWRKRWRKHRWRKRWRK | >53 | 40 | >53 |
| MU_37* | SEQ ID NO. 91 | RWRKRWRKRWRKRWRK | 23 | 35 | 23 |
| MU_69 | SEQ ID NO. 92 | RWRKRGRKRWRKRGRK | >53 | 27 | |
| MU_71 | SEQ ID NO. 93 | RWRKRWRKRWRKRWRK | 28 | 18.5 | |
| MU_73 | SEQ ID NO. 94 | RKRGWKWRKRGWKW | 42.5 | 22 | |
| MU_74 | SEQ ID NO. 95 | RLTRKRGRLTRKRG | 31 | >53 | |
| MU 84 | SEQ ID No. 98 | RWRKRWRWRKRWRWRKRW | 53 | 15 | |

From Table 8, it will be seen that the peptides in accordance with the present invention show antibacterial activity against at least one, if not two, and if not all three, of the three different bacterial strains evaluated. In particular, MU 24, MU 28, MU 37, MU 73, MU 30, and MU 32 are all particularly effective.

It will be appreciated that peptides which do not exhibit antibacterial activity either (i) are not tandem repeats; (ii) do not comprise at least two RKR motifs; or (iii) consist of amino acid substitutions which are not allowed or provided by in the formulae provided herein.

MU 84 is an example of a trimer, i.e. a tandem repeat comprising three monomers.

---

The invention claimed is:

1. A method of treating a bacterial infection in a subject, comprising:
providing a composition comprising a polypeptide and a pharmaceutically acceptable vehicle,
wherein the polypeptide comprises a tandem dimer repeat of a nonapeptide selected from the group consisting of: SEQ ID NO:1, SEQ ID NO:2, and SEQ ID NO:96, or the polypeptide comprises a tandem repeat of the nonapeptide wherein at least one amino acid residue, other than RKR motifs, of the polypeptide is replaced by an Arginine (R), Tyrosine (Y), Methionine (M), Isoleucine (I), Phenylalanine (F), Tryptophan (W); and
administering said composition to said subject.

2. The method of claim 1, wherein the nonapeptide is derived from a HSPG receptor binding region of apolipoprotein B or apolipoprotein E.

3. The method of claim 1, wherein the nonapeptide is derived from an apolipoprotein B LDL receptor binding domain cluster B, or from an apolipoprotein E LDL receptor binding domain cluster B.

4. The method of claim 1, wherein the polypeptide comprises at least two RKR motifs.

5. The method of claim 1, wherein the replaced or substituted residue is the first, second, third, seventh, eighth, ninth, tenth, eleventh, twelfth, sixteenth, seventeenth or eighteenth residue of the polypeptide.

6. The method of claim 1, wherein the at least one amino acid substitution is a Phenylalanine (F) residue or a Tryptophan (W) residue.

7. The method of claim 1, wherein the polypeptide comprises: a repeat of the peptide apoE$_{141-149}$, or a repeat of a variant of the peptide apoE$_{141-149}$ in which at least one Leucine (L) residue is replaced by Tryptophan (W), Arginine (R), Lysine (K), Tyrosine (Y) or Phenylalanine (F).

8. A method of treating a bacterial infection in a subject, comprising:
providing a composition comprising a polypeptide comprising a repeat of the peptide apoE$_{141-149}$ (SEQ ID NO:1), or a repeat of a variant or peptide apoE$_{141-149}$ in which at least one Leucine (L) residue is replaced by Tryptophan (W), Arginine (R), Lysine (K), Tyrosine (Y) or Phenylalanine (F), and a pharmaceutically acceptable vehicle; and
administering said composition to said subject.

9. The method of claim 8, wherein the polypeptide comprises a repeat of apoE$_{141-149}$ (SEQ ID NO:1), characterised in that at least one Leucine (L) residue is replaced by a Tryptophan (W), or a Phenylalanine (F) residue.

10. The method of claim 8, wherein the tandem repeat comprises at least two substitutions independently selected from Tryptophan (W), Arginine (R), Lysine (K), Tyrosine (Y), or Phenylalanine (F) substitutions.

11. The method of claim 1, wherein the polypeptide comprises the amino acid sequence: LRKLRKRLLLRKLRKRLL (SEQ ID NO:6); WRKWRKRWWWRKWRKRWW (SEQ ID NO:7); WRKWRKRWWLRKLRKRLL (SEQ ID NO:9); YRKYRKRYYYRKYRKRYY (SEQ ID NO: 10); FRKFRKRFFFRKFRKRFF (SEQ ID NO:48); WRKWRKRWWFRKWRKRWW (SEQ ID NO:65); WRKWRKRFFWRKWRKRFF (SEQ ID NO:66); LRKLRKRLLRLRKLRKRLLR (SEQ ID NO:68); WRKWRKRWWRWRKWRKRWWR (SEQ ID NO:69); LRKLRKRLLWRKWRKRWW (SEQ ID NO:70); LRKLLRKRLLLRKLRKRWW (SEQ ID NO:71); LRKLRKRLLWRKWRKRLL (SEQ ID NO:72); WRKRLLLRKLRKRLL (SEQ ID NO:73); WRKLRKRLLLRKLRKRLL (SEQ ID NO:74); or WRKWRKRWFRKFRKRFF (SEQ ID NO:76).

12. The method of claim 1, wherein the polypeptide comprises repeats of a peptide derived from an HSPG receptor binding region of apoB.

13. The method of claim 1, wherein the nonapeptide is derived from an HSPG receptor binding region of apolipoprotein B.

14. The method of claim 12, wherein the polypeptide is derived from an apolipoprotein B LDL receptor binding domain cluster B.

15. The method of claim 13, wherein the polypeptide comprises a repeat of apoB$_{3359-3367}$ (SEQ ID NO:2).

16. The method of claim 13, wherein the polypeptide comprises at least two RKR motifs.

17. A method of treating a bacterial infection in a subject, comprising:
providing a composition comprising a polypeptide and a pharmaceutically acceptable vehicle, wherein the polypeptide has the sequence of RLTRKRGLKRLTRKRGLK (SEQ ID NO:12) wherein at least one amino acid residue, other than the RKR mot has been replaced by a Glycine (G), Threonine (T), Histidine (H), Tryptophan (W), Arginine (R) or Leucine (L) residue; and
administering said composition to said subject.

18. The method of claim 17, wherein the at least one amino acid residue has been replaced by a Tryptophan (W), Arginine (R) or Leucine (L).

19. The method of claim 13, wherein the polypeptide is: RTRKRGRRTRKRGR (SEQ ID NO:13); LRKRKRLLRKRKRL (SEQ ID NO:14); LRKRKRLRKLRKRKRLRK (SEQ ID NO: 15); WRWRKRWRKWRWRKRWRK (SEQ ID NO:16); LLRKRLKRLLLRKRLKRL (SEQ ID NO:80); RRWRKRWRKWRWRKRWRK (SEQ ID NO:83); KRWRKRWRKWRWRKRWRK (SEQ ID NO:84); LRWRKRWRKWRWRKRWRK (SEQ ID NO:85); HRWRKRWRKWRWRKRWRK (SEQ ID NO:86); RWRWRKRWRWRKRWRK (SEQ ID NO:87); RRWRKRWRKRRWRKRWRK (SEQ ID NO:88); LRWRKRWRKLRWRKRWRK (SEQ ID NO:89); HRWRKRWRKHRWRKRWRK (SEQ ID NO:90); RWRKRWRKRWRKRWRK (SEQ ID NO:91); RWRKRGRKRWRKRGRK (SEQ ID NO:92); RWRKRWRKRWRKRWRK (SEQ ID NO:93); RKRGWKWRKRGWKW (SEQ ID NO:94); or RLTRKRGRLTRKRG (SEQ ID NO:95).

20. The method of claim 13, wherein the polypeptide has the sequence of RLTRKRGLKRLTRKRGLK (SEQ ID NO:12).

21. The method of claim 1, wherein said bacterial infection is a *Staphylococcus* Pseudomonadales or Streptococci infection.

22. A method of reducing the likelihood of and/or treating bacterial contamination comprising:
providing a composition comprising a polypeptide and a pharmaceutically acceptable vehicle, wherein the polypeptide comprises a tandem dimer repeat of a nonapeptide selected from the group consisting of: SEQ ID NO:1, SEQ ID NO:2, and SEQ ID NO:96, or the polypeptide comprises a tandem repeat of the nonapeptide wherein at least one amino acid residue, other than RKR motifs, of the polypeptide is replaced by an Arginine (R), Tyrosine (Y), Methionine (M), Isoleucine (I), Phenylalanine (F), Tryptophan (W); and
coating an object or a surface in need thereof with an amount of said composition in an amount effective for killing bacteria or reducing the growth of bacteria.

23. The method according to claim 22 wherein said object is selected from the group consisting of medical devices, lenses, contact lenses, catheters, stents, wound healing dressings, contraceptives, surgical implants and replacement joints.

24. The method according to claim 22 wherein said surface is selected from the group consisting of hospital ward surfaces, operating theatre surfaces, kitchen surfaces and sanitary surfaces.

25. The method of claim 8, wherein the polypeptide comprises the amino acid sequence: LRKLRKRLLLRKLRKRLL (SEQ ID NO:6); WRKWRKRWWWRKWRKRWW (SEQ ID NO:7); WRKWRKRWWLRKLRKRLL (SEQ ID NO:9); YRKYRKRYYYRKYRKRYY (SEQ ID NO:10); FRKFRKRFFFRKFRKRFF (SEQ ID NO:48); WRKWRKRWWFRKWRKRWW (SEQ ID NO:65); WRKWRKRFFWRKWRKRFF (SEQ ID NO:66); LRKLRKRLLWRKWRKRWW (SEQ ID NO:70); LRKLRKRLLLRKLRKRWW (SEQ ID NO:71); LRKLRKRLLWRKWRKRLL (SEQ ID NO:72); WRKWRKRLLLRKLRKRLL (SEQ ID NO:73); WRKLRKRLLLLRKLRKRLL (SEQ ID NO:74); or WRKWRKRWWFRKFRKRFF (SEQ ID NO:76).

26. The method of claim 13, wherein the polypeptide is derived from an apolipoprotein B LDL receptor binding domain cluster B.

27. The method of claim 8, wherein said bacterial infection is a *Staphylococcus* Pseudomonadales or Streptococci infection.

28. The method of claim 13, wherein said bacterial infection is a *Staphylococcus* Pseudomonadales or Streptococci infection.

29. The method of claim 22, wherein the object is a contact lens.

* * * * *

SEQUENCE LISTING

<160> NUMBER OF SEQ ID NOS: 98

<210> SEQ ID NO 1
<211> LENGTH: 9
<212> TYPE: PRT
<213> ORGANISM: Homo sapiens

<400> SEQUENCE: 1

Leu Arg Lys Leu Arg Lys Arg Leu Leu
1               5

<210> SEQ ID NO 2
<211> LENGTH: 9
<212> TYPE: PRT
<213> ORGANISM: Homo sapiens

<400> SEQUENCE: 2

```
Arg Leu Thr Arg Lys Arg Gly Leu Lys
1               5

<210> SEQ ID NO 3
<211> LENGTH: 15
<212> TYPE: PRT
<213> ORGANISM: Homo sapiens

<400> SEQUENCE: 3

Leu Arg Lys Arg Leu Leu Leu Arg Lys Leu Arg Lys Arg Leu Leu
1               5                   10                  15

<210> SEQ ID NO 4
<211> LENGTH: 22
<212> TYPE: PRT
<213> ORGANISM: Homo sapiens

<400> SEQUENCE: 4

Gln Ser Thr Glu Glu Leu Arg Val Arg Leu Ala Ser His Leu Arg Lys
1               5                   10                  15

Leu Arg Lys Arg Leu Leu
            20

<210> SEQ ID NO 5
<211> LENGTH: 30
<212> TYPE: PRT
<213> ORGANISM: Homo sapiens

<400> SEQUENCE: 5

Leu Arg Val Arg Leu Ala Ser His Leu Arg Lys Leu Arg Lys Arg Leu
1               5                   10                  15

Leu Arg Asp Ala Asp Asp Leu Gln Lys Arg Leu Ala Val Tyr
            20                  25                  30

<210> SEQ ID NO 6
<211> LENGTH: 18
<212> TYPE: PRT
<213> ORGANISM: Homo sapiens

<400> SEQUENCE: 6

Leu Arg Lys Leu Arg Lys Arg Leu Leu Arg Lys Leu Arg Lys Arg
1               5                   10                  15

Leu Leu

<210> SEQ ID NO 7
<211> LENGTH: 18
<212> TYPE: PRT
<213> ORGANISM: Homo sapiens

<400> SEQUENCE: 7

Trp Arg Lys Trp Arg Lys Arg Trp Trp Arg Lys Trp Arg Lys Arg
1               5                   10                  15

Trp Trp

<210> SEQ ID NO 8
<211> LENGTH: 14
<212> TYPE: PRT
<213> ORGANISM: Homo sapiens

<400> SEQUENCE: 8

Trp Arg Lys Trp Arg Lys Arg Trp Arg Lys Trp Arg Lys Arg
1               5                   10
```

-continued

```
<210> SEQ ID NO 9
<211> LENGTH: 18
<212> TYPE: PRT
<213> ORGANISM: Homo sapiens

<400> SEQUENCE: 9

Trp Arg Lys Trp Arg Lys Arg Trp Trp Leu Arg Lys Leu Arg Lys Arg
1               5                   10                  15

Leu Leu

<210> SEQ ID NO 10
<211> LENGTH: 18
<212> TYPE: PRT
<213> ORGANISM: Homo sapiens

<400> SEQUENCE: 10

Tyr Arg Lys Tyr Arg Lys Arg Tyr Tyr Arg Lys Tyr Arg Lys Arg
1               5                   10                  15

Tyr Tyr

<210> SEQ ID NO 11
<211> LENGTH: 14
<212> TYPE: PRT
<213> ORGANISM: Homo sapiens

<400> SEQUENCE: 11

Leu Arg Lys Leu Arg Lys Arg Leu Arg Lys Leu Arg Lys Arg
1               5                   10

<210> SEQ ID NO 12
<211> LENGTH: 18
<212> TYPE: PRT
<213> ORGANISM: Homo sapiens

<400> SEQUENCE: 12

Arg Leu Thr Arg Lys Arg Gly Leu Lys Arg Leu Thr Arg Lys Arg Gly
1               5                   10                  15

Leu Lys

<210> SEQ ID NO 13
<211> LENGTH: 14
<212> TYPE: PRT
<213> ORGANISM: Homo sapiens

<400> SEQUENCE: 13

Arg Thr Arg Lys Arg Gly Arg Thr Arg Lys Arg Gly Arg
1               5                   10

<210> SEQ ID NO 14
<211> LENGTH: 14
<212> TYPE: PRT
<213> ORGANISM: Homo sapiens

<400> SEQUENCE: 14

Leu Arg Lys Arg Lys Arg Leu Leu Arg Lys Arg Lys Arg Leu
1               5                   10

<210> SEQ ID NO 15
<211> LENGTH: 18
<212> TYPE: PRT
<213> ORGANISM: Homo sapiens

<400> SEQUENCE: 15

Leu Arg Lys Arg Lys Arg Leu Arg Lys Leu Arg Lys Arg Lys Arg Leu
```

```
1               5                   10                  15
Arg Lys

<210> SEQ ID NO 16
<211> LENGTH: 18
<212> TYPE: PRT
<213> ORGANISM: Homo sapiens

<400> SEQUENCE: 16

Trp Arg Trp Arg Lys Arg Trp Arg Lys Trp Arg Trp Arg Lys Arg Trp
1               5                   10                  15

Arg Lys

<210> SEQ ID NO 17

<400> SEQUENCE: 17

000

<210> SEQ ID NO 18

<400> SEQUENCE: 18

000

<210> SEQ ID NO 19
<211> LENGTH: 37
<212> TYPE: PRT
<213> ORGANISM: Homo sapiens

<400> SEQUENCE: 19

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 20
<211> LENGTH: 30
<212> TYPE: PRT
<213> ORGANISM: Homo sapiens

<400> SEQUENCE: 20

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30

<210> SEQ ID NO 21
<211> LENGTH: 39
<212> TYPE: PRT
<213> ORGANISM: Sus sp.

<400> SEQUENCE: 21

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
                20                  25                  30

Arg Phe Pro Pro Arg Phe Pro
            35
```

```
<210> SEQ ID NO 22
<211> LENGTH: 13
<212> TYPE: PRT
<213> ORGANISM: Bos sp.

<400> SEQUENCE: 22

Ile Leu Pro Trp Lys Trp Pro Trp Trp Pro Trp Arg Arg
1               5                   10

<210> SEQ ID NO 23
<211> LENGTH: 27
<212> TYPE: DNA
<213> ORGANISM: Homo sapiens

<400> SEQUENCE: 23
cttcgtaaac ttcgtaaacg tcttctt                                        27

<210> SEQ ID NO 24
<211> LENGTH: 27
<212> TYPE: DNA
<213> ORGANISM: Homo sapiens

<400> SEQUENCE: 24
cgtcttactc gtaaacgtgg tcttaaa                                        27

<210> SEQ ID NO 25
<211> LENGTH: 45
<212> TYPE: DNA
<213> ORGANISM: Homo sapiens

<400> SEQUENCE: 25
cttcgtaaac gtcttcttct tcgtaaactt cgtaaacgtc ttctt                    45

<210> SEQ ID NO 26
<211> LENGTH: 66
<212> TYPE: DNA
<213> ORGANISM: Homo sapiens

<400> SEQUENCE: 26
caatctactg aagaacttcg tgttcgtctt gctagtcatc ttcgtaaact tcgtaaacgt    60
cttctt                                                               66

<210> SEQ ID NO 27
<211> LENGTH: 180
<212> TYPE: DNA
<213> ORGANISM: Homo sapiens

<400> SEQUENCE: 27
cttcgtgttc gtcttgctag tcatcttcgt aaacttcgta acgtcttct tcgtgatgct     60 gatgatcttc aaaaacgtct tgctgtttat cttcgtgttc gtcttgctag tcatcttcgt   120
aaacttcgta acgtcttct tcgtgatgct gatgatcttc aaaaacgtct tgctgtttat    180

<210> SEQ ID NO 28
<211> LENGTH: 54
<212> TYPE: DNA
<213> ORGANISM: Homo sapiens

<400> SEQUENCE: 28
cttcgtaaac ttcgtaaacg tcttcttctt cgtaaacttc gtaaacgtct tctt          54

<210> SEQ ID NO 29
<211> LENGTH: 54
<212> TYPE: DNA
```

<213> ORGANISM: Homo sapiens

<400> SEQUENCE: 29
tggcgtaaat ggcgtaaacg ttggtggtgg cgtaaatggc gtaaacgttg gtgg    54

<210> SEQ ID NO 30
<211> LENGTH: 48
<212> TYPE: DNA
<213> ORGANISM: Homo sapiens

<400> SEQUENCE: 30
tggcgtaaat ggcgtaaacg ttggtggcgt aaatggcgta aacgttgg    48

<210> SEQ ID NO 31
<211> LENGTH: 54
<212> TYPE: DNA
<213> ORGANISM: Homo sapiens

<400> SEQUENCE: 31
tggcgtaaat ggcgtaaacg ttggtggctt cgtaaacttc gtaaacgtct tctt    54

<210> SEQ ID NO 32
<211> LENGTH: 54
<212> TYPE: DNA
<213> ORGANISM: Homo sapiens

<400> SEQUENCE: 32
tatcgtaaat atcgtaaacg ttattattat cgtaaatatc gtaaacgtta ttat    54

<210> SEQ ID NO 33
<211> LENGTH: 42
<212> TYPE: DNA
<213> ORGANISM: Homo sapiens

<400> SEQUENCE: 33
cttcgtaaac ttcgtaaacg tcttcgtaaa cttcgtaaac gt    42

<210> SEQ ID NO 34
<211> LENGTH: 54
<212> TYPE: DNA
<213> ORGANISM: Homo sapiens

<400> SEQUENCE: 34
cgtcttactc gtaaacgtgg tcttaaacgt cttactcgta aacgtggtct taaa    54

<210> SEQ ID NO 35
<211> LENGTH: 42
<212> TYPE: DNA
<213> ORGANISM: Homo sapiens

<400> SEQUENCE: 35
cgtactcgta aacgtggtcg tcgtactcgt aaacgtggtc gt    42

<210> SEQ ID NO 36
<211> LENGTH: 42
<212> TYPE: DNA
<213> ORGANISM: Homo sapiens

<400> SEQUENCE: 36
cttcgtaaac gtaaacgtct tcttcgtaaa cgtaaacgtc tt    42

<210> SEQ ID NO 37
<211> LENGTH: 54
<212> TYPE: DNA

<213> ORGANISM: Homo sapiens

<400> SEQUENCE: 37
cttcgtaaac gtaaacgtct tcgtaaactt cgtaaacgta aacgtcttcg taaa        54

<210> SEQ ID NO 38
<211> LENGTH: 54
<212> TYPE: DNA
<213> ORGANISM: Homo sapiens

<400> SEQUENCE: 38
tggcgttggc gtaaacgttg gcgtaaatgg cgttggcgta aacgttggcg taaa        54

<210> SEQ ID NO 39
<211> LENGTH: 18
<212> TYPE: PRT
<213> ORGANISM: Homo sapiens

<400> SEQUENCE: 39

Glu Arg Lys Glu Arg Lys Arg Glu Glu Glu Arg Lys Glu Arg Lys Arg
1               5                   10                  15

Glu Glu

<210> SEQ ID NO 40

<400> SEQUENCE: 40

000

<210> SEQ ID NO 41
<211> LENGTH: 18
<212> TYPE: PRT
<213> ORGANISM: Homo sapiens

<400> SEQUENCE: 41

Ala Arg Lys Ala Arg Lys Arg Ala Ala Ala Arg Lys Ala Arg Lys Arg
1               5                   10                  15

Ala Ala

<210> SEQ ID NO 42
<211> LENGTH: 18
<212> TYPE: PRT
<213> ORGANISM: Homo sapiens

<400> SEQUENCE: 42

Met Arg Lys Met Arg Lys Arg Met Met Met Arg Lys Met Arg Lys Arg
1               5                   10                  15

Met Met

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47
<211> LENGTH: 30
<212> TYPE: PRT
<213> ORGANISM: Homo sapiens

<400> SEQUENCE: 47

Leu Arg Val Arg Leu Ala Ser His Leu Arg Lys Leu Arg Lys Arg Leu
1               5                   10                  15

Leu Arg Asp Ala Asp Asp Leu Gln Lys Arg Leu Ala Val Tyr
            20                  25                  30

<210> SEQ ID NO 48
<211> LENGTH: 18
<212> TYPE: PRT
<213> ORGANISM: Homo sapiens

<400> SEQUENCE: 48

Phe Arg Lys Phe Arg Lys Arg Phe Phe Phe Arg Lys Phe Arg Lys Arg
1               5                   10                  15

Phe Phe

<210> SEQ ID NO 49
<211> LENGTH: 18
<212> TYPE: PRT
<213> ORGANISM: Homo sapiens

<400> SEQUENCE: 49

Ile Arg Lys Ile Arg Lys Arg Ile Ile Ile Arg Lys Ile Arg Lys Arg
1               5                   10                  15

Ile Ile

<210> SEQ ID NO 50
<211> LENGTH: 18
<212> TYPE: PRT
<213> ORGANISM: Homo sapiens

<400> SEQUENCE: 50

Gln Arg Lys Gln Arg Lys Arg Gln Gln Gln Arg Lys Gln Arg Lys Arg
1               5                   10                  15

Gln Gln

<210> SEQ ID NO 51
<211> LENGTH: 18
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

```
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 51
nrknrkrnnn rknrkrnn                                                   18

<210> SEQ ID NO 52
<211> LENGTH: 18
<212> TYPE: DNA
<213> ORGANISM: Homo sapiens

<400> SEQUENCE: 52
crkcrkrccc rkcrkrcc                                                   18

<210> SEQ ID NO 53
<211> LENGTH: 18
<212> TYPE: DNA
<213> ORGANISM: Homo sapiens

<400> SEQUENCE: 53
srksrkrsss rksrkrss                                                   18

<210> SEQ ID NO 54
<211> LENGTH: 18
<212> TYPE: DNA
<213> ORGANISM: Homo sapiens

<400> SEQUENCE: 54
vrkvrkrvvv rkvrkrvv                                                   18

<210> SEQ ID NO 55
<211> LENGTH: 18
<212> TYPE: PRT
<213> ORGANISM: Homo sapiens

<400> SEQUENCE: 55

Thr Arg Lys Thr Arg Lys Arg Thr Thr Thr Arg Lys Thr Arg Lys Arg
1               5                   10                  15

Thr Thr

<210> SEQ ID NO 56
<211> LENGTH: 18
<212> TYPE: DNA
<213> ORGANISM: Homo sapiens

<400> SEQUENCE: 56
rrkrrkrrrr rkrrkrrr                                                   18

<210> SEQ ID NO 57
<211> LENGTH: 18
<212> TYPE: PRT
<213> ORGANISM: Homo sapiens

<400> SEQUENCE: 57

Gly Arg Lys Gly Arg Lys Arg Gly Gly Gly Arg Lys Gly Arg Lys Arg
1               5                   10                  15

Gly Gly
```

```
<210> SEQ ID NO 58
<211> LENGTH: 18
<212> TYPE: PRT
<213> ORGANISM: Homo sapiens

<400> SEQUENCE: 58

Lys Arg Lys Lys Arg Lys Arg Lys Lys Lys Arg Lys Lys Arg Lys Arg
1               5                   10                  15

Lys Lys

<210> SEQ ID NO 59
<211> LENGTH: 18
<212> TYPE: PRT
<213> ORGANISM: Homo sapiens

<400> SEQUENCE: 59

Asp Arg Lys Asp Arg Lys Arg Asp Asp Asp Arg Lys Asp Arg Lys Arg
1               5                   10                  15

Asp Asp

<210> SEQ ID NO 60
<211> LENGTH: 18
<212> TYPE: PRT
<213> ORGANISM: Homo sapiens

<400> SEQUENCE: 60

Pro Arg Lys Pro Arg Lys Arg Pro Pro Pro Arg Lys Pro Arg Lys Arg
1               5                   10                  15

Pro Pro

<210> SEQ ID NO 61
<211> LENGTH: 18
<212> TYPE: PRT
<213> ORGANISM: Homo sapiens

<400> SEQUENCE: 61

Met Arg Lys Leu Arg Lys Arg Leu Met Met Arg Lys Leu Arg Lys Arg
1               5                   10                  15

Leu Met

<210> SEQ ID NO 62
<211> LENGTH: 9
<212> TYPE: PRT
<213> ORGANISM: Homo sapiens

<400> SEQUENCE: 62

Leu Arg Lys Leu Arg Lys Arg Leu Leu
1               5

<210> SEQ ID NO 63
<211> LENGTH: 17
<212> TYPE: PRT
<213> ORGANISM: Homo sapiens

<400> SEQUENCE: 63

Trp Arg Lys Trp Arg Lys Arg Trp Trp Arg Lys Trp Arg Lys Arg Trp
1               5                   10                  15

Trp

<210> SEQ ID NO 64
<211> LENGTH: 15
<212> TYPE: PRT
<213> ORGANISM: Homo sapiens
```

```
<400> SEQUENCE: 64

Trp Arg Lys Trp Arg Lys Arg Trp Arg Lys Arg Trp
1               5                   10                  15

<210> SEQ ID NO 65
<211> LENGTH: 18
<212> TYPE: PRT
<213> ORGANISM: Homo sapiens

<400> SEQUENCE: 65

Trp Arg Lys Trp Arg Lys Arg Trp Trp Phe Arg Lys Trp Arg Lys
1               5                   10                  15

Trp Trp

<210> SEQ ID NO 66
<211> LENGTH: 18
<212> TYPE: PRT
<213> ORGANISM: Homo sapiens

<400> SEQUENCE: 66

Trp Arg Lys Trp Arg Lys Arg Phe Phe Trp Arg Lys Trp Arg Lys
1               5                   10                  15

Phe Phe

<210> SEQ ID NO 67
<211> LENGTH: 14
<212> TYPE: DNA
<213> ORGANISM: Homo sapiens

<400> SEQUENCE: 67 wrkwwrwrk rwwr                                                          14

<210> SEQ ID NO 68
<211> LENGTH: 20
<212> TYPE: PRT
<213> ORGANISM: Homo sapiens

<400> SEQUENCE: 68

Leu Arg Lys Leu Arg Lys Arg Leu Leu Arg Leu Arg Lys Leu Arg Lys
1               5                   10                  15

Arg Leu Leu Arg
            20

<210> SEQ ID NO 69
<211> LENGTH: 20
<212> TYPE: PRT
<213> ORGANISM: Homo sapiens

<400> SEQUENCE: 69

Trp Arg Lys Trp Arg Lys Arg Trp Trp Arg Trp Arg Lys Trp Arg Lys
1               5                   10                  15

Arg Trp Trp Arg
            20

<210> SEQ ID NO 70
<211> LENGTH: 18
<212> TYPE: PRT
<213> ORGANISM: Homo sapiens

<400> SEQUENCE: 70

Leu Arg Lys Leu Arg Lys Arg Leu Leu Trp Arg Lys Trp Arg Lys Arg
1               5                   10                  15
```

Trp Trp

<210> SEQ ID NO 71
<211> LENGTH: 18
<212> TYPE: PRT
<213> ORGANISM: Homo sapiens

<400> SEQUENCE: 71

Leu Arg Lys Leu Arg Lys Arg Leu Leu Leu Arg Lys Leu Arg Lys Arg
1               5                   10                  15

Trp Trp

<210> SEQ ID NO 72
<211> LENGTH: 18
<212> TYPE: PRT
<213> ORGANISM: Homo sapiens

<400> SEQUENCE: 72

Leu Arg Lys Leu Arg Lys Arg Leu Leu Trp Arg Lys Trp Arg Lys Arg
1               5                   10                  15

Leu Leu

<210> SEQ ID NO 73
<211> LENGTH: 18
<212> TYPE: PRT
<213> ORGANISM: Homo sapiens

<400> SEQUENCE: 73

Trp Arg Lys Trp Arg Lys Arg Leu Leu Leu Arg Lys Leu Arg Lys Arg
1               5                   10                  15

Leu Leu

<210> SEQ ID NO 74
<211> LENGTH: 18
<212> TYPE: PRT
<213> ORGANISM: Homo sapiens

<400> SEQUENCE: 74

Trp Arg Lys Leu Arg Lys Arg Leu Leu Leu Arg Lys Leu Arg Lys Arg
1               5                   10                  15

Leu Leu

<210> SEQ ID NO 75
<211> LENGTH: 17
<212> TYPE: PRT
<213> ORGANISM: Homo sapiens

<400> SEQUENCE: 75

Trp Arg Lys Trp Arg Lys Phe Phe Phe Arg Lys Trp Arg Lys Arg Trp
1               5                   10                  15

Trp

<210> SEQ ID NO 76
<211> LENGTH: 18
<212> TYPE: PRT
<213> ORGANISM: Homo sapiens

<400> SEQUENCE: 76

Trp Arg Lys Trp Arg Lys Arg Trp Trp Phe Arg Lys Phe Arg Lys Arg
1               5                   10                  15

Phe Phe

-continued

<210> SEQ ID NO 77
<211> LENGTH: 12
<212> TYPE: PRT
<213> ORGANISM: Homo sapiens

<400> SEQUENCE: 77

Leu Arg Lys Leu Arg Lys Arg Leu Leu Leu Arg Lys
1               5                   10

<210> SEQ ID NO 78
<211> LENGTH: 18
<212> TYPE: PRT
<213> ORGANISM: Homo sapiens

<400> SEQUENCE: 78

Arg Leu Leu Arg Leu Leu Arg Leu Leu Arg Leu Leu Arg Leu Leu Arg
1               5                   10                  15

Leu Leu

<210> SEQ ID NO 79

<400> SEQUENCE: 79

000

<210> SEQ ID NO 80
<211> LENGTH: 18
<212> TYPE: PRT
<213> ORGANISM: Homo sapiens

<400> SEQUENCE: 80

Leu Leu Arg Lys Arg Leu Lys Arg Leu Leu Leu Arg Lys Arg Leu Lys
1               5                   10                  15

Arg Leu

<210> SEQ ID NO 81
<211> LENGTH: 18
<212> TYPE: PRT
<213> ORGANISM: Homo sapiens

<400> SEQUENCE: 81

Trp Arg Trp Arg Arg Arg Trp Arg Lys Trp Arg Trp Arg Arg Arg Trp
1               5                   10                  15

Arg Lys

<210> SEQ ID NO 82
<211> LENGTH: 18
<212> TYPE: PRT
<213> ORGANISM: Homo sapiens

<400> SEQUENCE: 82

Trp Arg Trp Lys Lys Lys Trp Arg Lys Trp Arg Trp Lys Lys Lys Trp
1               5                   10                  15

Arg Lys

<210> SEQ ID NO 83
<211> LENGTH: 18
<212> TYPE: PRT
<213> ORGANISM: Homo sapiens

<400> SEQUENCE: 83

Arg Arg Trp Arg Lys Arg Trp Arg Lys Trp Arg Trp Arg Lys Arg Trp

```
1               5                   10                  15
Arg Lys

<210> SEQ ID NO 84
<211> LENGTH: 18
<212> TYPE: PRT
<213> ORGANISM: Homo sapiens

<400> SEQUENCE: 84

Lys Arg Trp Arg Lys Arg Trp Arg Lys Trp Arg Trp Arg Lys Arg Trp
1               5                   10                  15

Arg Lys

<210> SEQ ID NO 85
<211> LENGTH: 18
<212> TYPE: PRT
<213> ORGANISM: Homo sapiens

<400> SEQUENCE: 85

Leu Arg Trp Arg Lys Arg Trp Arg Lys Trp Arg Trp Arg Lys Arg Trp
1               5                   10                  15

Arg Lys

<210> SEQ ID NO 86
<211> LENGTH: 18
<212> TYPE: PRT
<213> ORGANISM: Homo sapiens

<400> SEQUENCE: 86

His Arg Trp Arg Lys Arg Trp Arg Lys Trp Arg Trp Arg Lys Arg Trp
1               5                   10                  15

Arg Lys

<210> SEQ ID NO 87
<211> LENGTH: 17
<212> TYPE: PRT
<213> ORGANISM: Homo sapiens

<400> SEQUENCE: 87

Arg Trp Arg Lys Arg Trp Arg Lys Trp Arg Trp Arg Lys Arg Trp Arg
1               5                   10                  15

Lys

<210> SEQ ID NO 88
<211> LENGTH: 18
<212> TYPE: PRT
<213> ORGANISM: Homo sapiens

<400> SEQUENCE: 88

Arg Arg Trp Arg Lys Arg Trp Arg Lys Arg Trp Arg Lys Arg Trp Arg
1               5                   10                  15

Arg Lys

<210> SEQ ID NO 89
<211> LENGTH: 18
<212> TYPE: PRT
<213> ORGANISM: Homo sapiens

<400> SEQUENCE: 89

Leu Arg Trp Arg Lys Arg Trp Arg Lys Leu Trp Arg Lys Arg Trp
1               5                   10                  15
```

Arg Lys

<210> SEQ ID NO 90
<211> LENGTH: 18
<212> TYPE: PRT
<213> ORGANISM: Homo sapiens

<400> SEQUENCE: 90

His Arg Trp Arg Lys Arg Trp Arg Lys His Arg Trp Arg Lys Arg Trp
1               5                   10                  15
Arg Lys

<210> SEQ ID NO 91
<211> LENGTH: 16
<212> TYPE: PRT
<213> ORGANISM: Homo sapiens

<400> SEQUENCE: 91

Arg Trp Arg Lys Arg Trp Arg Lys Arg Trp Lys Arg Trp Arg Lys
1               5                   10                  15

<210> SEQ ID NO 92
<211> LENGTH: 16
<212> TYPE: PRT
<213> ORGANISM: Homo sapiens

<400> SEQUENCE: 92

Arg Trp Arg Lys Arg Gly Arg Lys Arg Trp Arg Lys Arg Gly Arg Lys
1               5                   10                  15

<210> SEQ ID NO 93
<211> LENGTH: 16
<212> TYPE: PRT
<213> ORGANISM: Homo sapiens

<400> SEQUENCE: 93

Arg Trp Arg Lys Arg Trp Arg Lys Arg Trp Arg Lys Arg Trp Arg Lys
1               5                   10                  15

<210> SEQ ID NO 94
<211> LENGTH: 14
<212> TYPE: PRT
<213> ORGANISM: Homo sapiens

<400> SEQUENCE: 94

Arg Lys Arg Gly Trp Lys Trp Arg Lys Arg Gly Trp Lys Trp
1               5                   10

<210> SEQ ID NO 95
<211> LENGTH: 14
<212> TYPE: PRT
<213> ORGANISM: Homo sapiens

<400> SEQUENCE: 95

Arg Leu Thr Arg Lys Arg Gly Arg Leu Thr Arg Lys Arg Gly
1               5                   10

<210> SEQ ID NO 96
<211> LENGTH: 9
<212> TYPE: PRT
<213> ORGANISM: Homo sapiens

<400> SEQUENCE: 96

Leu Arg Thr Arg Lys Arg Gly Arg Lys
1               5

```
<210> SEQ ID NO 97
<211> LENGTH: 60
<212> TYPE: PRT
<213> ORGANISM: Homo sapiens

<400> SEQUENCE: 97

Leu Arg Val Arg Leu Ala Ser His Leu Arg Lys Leu Arg Lys Arg Leu
1               5                   10                  15

Leu Arg Asp Ala Asp Asp Leu Gln Lys Arg Leu Ala Val Tyr Leu Arg
                20                  25                  30

Val Arg Leu Ala Ser His Leu Arg Lys Leu Arg Lys Arg Leu Leu Arg
            35                  40                  45

Asp Ala Asp Asp Leu Gln Lys Arg Leu Ala Val Tyr
        50                  55                  60

<210> SEQ ID NO 98
<211> LENGTH: 18
<212> TYPE: PRT
<213> ORGANISM: Homo sapiens

<400> SEQUENCE: 98

Arg Trp Arg Lys Arg Trp Arg Trp Arg Lys Arg Trp Arg Trp Arg Lys
1               5                   10                  15

Arg Trp
```